United States Patent
Alderete, Jr. et al.

(10) Patent No.: US 9,839,753 B2
(45) Date of Patent: Dec. 12, 2017

(54) SYSTEMS FOR MANAGING RESERVOIR CHAMBER PRESSURE

(71) Applicant: MEDTRONIC MINIMED, INC., Northridge, CA (US)

(72) Inventors: Juan M. Alderete, Jr., Granada Hills, CA (US); Andrew E. Weaver, Granada Hills, CA (US); Matthew William Yavorsky, Huntington Beach, CA (US); Benjamin A. Grover, Granada Hills, CA (US); Pablo Vazquez, Porter Ranch, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 581 days.

(21) Appl. No.: 14/497,878

(22) Filed: Sep. 26, 2014

(65) Prior Publication Data
US 2016/0089505 A1     Mar. 31, 2016

(51) Int. Cl.
*A61M 5/48* (2006.01)
*A61M 5/38* (2006.01)
*A61M 5/145* (2006.01)
*A61M 5/142* (2006.01)

(52) U.S. Cl.
CPC .......... *A61M 5/482* (2013.01); *A61M 5/1452* (2013.01); *A61M 5/14244* (2013.01); *A61M 5/385* (2013.01); *A61M 5/484* (2013.01)

(58) Field of Classification Search
CPC .............. A61M 5/482; A61M 5/14244; A61M 5/1452; A61M 5/385; A61M 5/484; A61M 5/14566; A61M 5/1458; A61M 5/1456; A61B 5/15003

USPC .......... 604/131, 151; 600/578, 573
See application file for complete search history.

(56) References Cited

U.S. PATENT DOCUMENTS

| | | |
|---|---|---|
| 3,631,847 A | 1/1972 | Hobbs, II |
| 4,000,741 A | 1/1977 | Binard et al. |
| 4,212,738 A | 7/1980 | Henne |
| 4,270,532 A | 6/1981 | Franetzki et al. |
| 4,282,872 A | 8/1981 | Franetzki et al. |
| 4,373,527 A | 2/1983 | Fischell |

(Continued)

FOREIGN PATENT DOCUMENTS

| | | |
|---|---|---|
| DE | 4329229 | 3/1995 |
| EP | 0319268 | 11/1988 |

(Continued)

OTHER PUBLICATIONS

PCT Search Report (PCT/US02/03299), dated Oct. 31, 2002, Medtronic Minimed, Inc.

(Continued)

*Primary Examiner* — Manuel Mendez
(74) *Attorney, Agent, or Firm* — Lorenz & Kopf, LLC

(57) ABSTRACT

Systems for managing pressure in a fluid reservoir chamber of a fluid infusion device are provided. For example, a fluid infusion device comprises a housing having a chamber for receiving a fluid reservoir. The fluid infusion device also comprises a drive system contained within the housing. A portion of the drive system is movable for dispensing fluid from the fluid reservoir. The fluid infusion device comprises a pressure management system at least partially defined in the portion of the drive system to vent air from the chamber.

11 Claims, 13 Drawing Sheets

(56) References Cited

U.S. PATENT DOCUMENTS

| | | | |
|---|---|---|---|
| 4,373,535 A * | 2/1983 | Martell | A61B 5/15003 600/578 |
| 4,395,259 A | 7/1983 | Prestele et al. | |
| 4,433,072 A | 2/1984 | Pusineri et al. | |
| 4,443,218 A | 4/1984 | DeCant, Jr. et al. | |
| 4,494,950 A | 1/1985 | Fischell | |
| 4,529,401 A * | 7/1985 | Leslie | A61M 5/1456 128/DIG. 1 |
| 4,542,532 A | 9/1985 | McQuilkin | |
| 4,550,731 A | 11/1985 | Batina et al. | |
| 4,559,037 A | 12/1985 | Franetzki et al. | |
| 4,562,751 A | 1/1986 | Nason et al. | |
| 4,671,288 A | 6/1987 | Gough | |
| 4,678,408 A | 7/1987 | Nason et al. | |
| 4,685,903 A | 8/1987 | Cable et al. | |
| 4,731,051 A | 3/1988 | Fischell | |
| 4,731,726 A | 3/1988 | Allen, III | |
| 4,781,798 A | 11/1988 | Gough | |
| 4,803,625 A | 2/1989 | Fu et al. | |
| 4,809,697 A | 3/1989 | Causey, III et al. | |
| 4,826,810 A | 5/1989 | Aoki | |
| 4,871,351 A | 10/1989 | Feingold | |
| 4,898,578 A | 2/1990 | Rubalcaba, Jr. | |
| 5,003,298 A | 3/1991 | Havel | |
| 5,011,468 A | 4/1991 | Lundquist et al. | |
| 5,019,974 A | 5/1991 | Beckers | |
| 5,050,612 A | 9/1991 | Matsumura | |
| 5,078,683 A | 1/1992 | Sancoff et al. | |
| 5,080,653 A | 1/1992 | Voss et al. | |
| 5,097,122 A | 3/1992 | Colman et al. | |
| 5,100,380 A | 3/1992 | Epstein et al. | |
| 5,101,814 A | 4/1992 | Palti | |
| 5,108,819 A | 4/1992 | Heller et al. | |
| 5,153,827 A | 10/1992 | Coutre et al. | |
| 5,165,407 A | 11/1992 | Wilson et al. | |
| 5,247,434 A | 9/1993 | Peterson et al. | |
| 5,262,035 A | 11/1993 | Gregg et al. | |
| 5,262,305 A | 11/1993 | Heller et al. | |
| 5,264,104 A | 11/1993 | Gregg et al. | |
| 5,264,105 A | 11/1993 | Gregg et al. | |
| 5,284,140 A | 2/1994 | Allen et al. | |
| 5,299,571 A | 4/1994 | Mastrototaro | |
| 5,307,263 A | 4/1994 | Brown | |
| 5,317,506 A | 5/1994 | Coutre et al. | |
| 5,320,725 A | 6/1994 | Gregg et al. | |
| 5,322,063 A | 6/1994 | Allen et al. | |
| 5,338,157 A | 8/1994 | Blomquist | |
| 5,339,821 A | 8/1994 | Fujimoto | |
| 5,341,291 A | 8/1994 | Roizen et al. | |
| 5,350,411 A | 9/1994 | Ryan et al. | |
| 5,356,786 A | 10/1994 | Heller et al. | |
| 5,357,427 A | 10/1994 | Langen et al. | |
| 5,368,562 A | 11/1994 | Blomquist et al. | |
| 5,370,622 A | 12/1994 | Livingston et al. | |
| 5,371,687 A | 12/1994 | Holmes, II et al. | |
| 5,376,070 A | 12/1994 | Purvis et al. | |
| 5,390,671 A | 2/1995 | Lord et al. | |
| 5,391,250 A | 2/1995 | Cheney, II et al. | |
| 5,403,700 A | 4/1995 | Heller et al. | |
| 5,411,647 A | 5/1995 | Johnson et al. | |
| 5,482,473 A | 1/1996 | Lord et al. | |
| 5,485,408 A | 1/1996 | Blomquist | |
| 5,497,772 A | 3/1996 | Schulman et al. | |
| 5,505,709 A | 4/1996 | Funderburk et al. | |
| 5,543,326 A | 8/1996 | Heller et al. | |
| 5,569,186 A | 10/1996 | Lord et al. | |
| 5,569,187 A | 10/1996 | Kaiser | |
| 5,573,506 A | 11/1996 | Vasko | |
| 5,582,593 A | 12/1996 | Hultman | |
| 5,586,553 A | 12/1996 | Halili et al. | |
| 5,593,390 A | 1/1997 | Castellano et al. | |
| 5,593,852 A | 1/1997 | Heller et al. | |
| 5,594,638 A | 1/1997 | Illiff | |
| 5,609,060 A | 3/1997 | Dent | |
| 5,626,144 A | 5/1997 | Tacklind et al. | |
| 5,630,710 A | 5/1997 | Tune et al. | |
| 5,643,212 A | 7/1997 | Coutre et al. | |
| 5,660,163 A | 8/1997 | Schulman et al. | |
| 5,660,176 A | 8/1997 | Iliff | |
| 5,665,065 A | 9/1997 | Colman et al. | |
| 5,665,222 A | 9/1997 | Heller et al. | |
| 5,685,844 A | 11/1997 | Marttila | |
| 5,687,734 A | 11/1997 | Dempsey et al. | |
| 5,704,366 A | 1/1998 | Tacklind et al. | |
| 5,750,926 A | 5/1998 | Schulman et al. | |
| 5,754,111 A | 5/1998 | Garcia | |
| 5,764,159 A | 6/1998 | Neftel | |
| 5,772,635 A | 6/1998 | Dastur et al. | |
| 5,779,665 A | 7/1998 | Mastrototaro et al. | |
| 5,788,669 A | 8/1998 | Peterson | |
| 5,791,344 A | 8/1998 | Schulman et al. | |
| 5,800,420 A | 9/1998 | Gross et al. | |
| 5,807,336 A | 9/1998 | Russo et al. | |
| 5,814,015 A | 9/1998 | Gargano et al. | |
| 5,822,715 A | 10/1998 | Worthington et al. | |
| 5,832,448 A | 11/1998 | Brown | |
| 5,840,020 A | 11/1998 | Heinonen et al. | |
| 5,861,018 A | 1/1999 | Feierbach et al. | |
| 5,868,669 A | 2/1999 | Iliff | |
| 5,871,465 A | 2/1999 | Vasko | |
| 5,879,163 A | 3/1999 | Brown et al. | |
| 5,885,245 A | 3/1999 | Lynch et al. | |
| 5,897,493 A | 4/1999 | Brown | |
| 5,899,855 A | 5/1999 | Brown | |
| 5,904,708 A | 5/1999 | Goedeke | |
| 5,913,310 A | 6/1999 | Brown | |
| 5,917,346 A | 6/1999 | Gord | |
| 5,918,603 A | 7/1999 | Brown | |
| 5,925,021 A | 7/1999 | Castellano et al. | |
| 5,933,136 A | 8/1999 | Brown | |
| 5,935,099 A | 8/1999 | Peterson et al. | |
| 5,940,801 A | 8/1999 | Brown | |
| 5,956,501 A | 9/1999 | Brown | |
| 5,960,403 A | 9/1999 | Brown | |
| 5,965,380 A | 10/1999 | Heller et al. | |
| 5,972,199 A | 10/1999 | Heller et al. | |
| 5,978,236 A | 11/1999 | Faberman et al. | |
| 5,997,476 A | 12/1999 | Brown | |
| 5,999,848 A | 12/1999 | Gord et al. | |
| 5,999,849 A | 12/1999 | Gord et al. | |
| 6,009,339 A | 12/1999 | Bentsen et al. | |
| 6,032,119 A | 2/2000 | Brown et al. | |
| 6,043,437 A | 3/2000 | Schulman et al. | |
| 6,081,736 A | 6/2000 | Colvin et al. | |
| 6,083,710 A | 7/2000 | Heller et al. | |
| 6,088,608 A | 7/2000 | Schulman et al. | |
| 6,101,478 A | 8/2000 | Brown | |
| 6,103,033 A | 8/2000 | Say et al. | |
| 6,119,028 A | 9/2000 | Schulman et al. | |
| 6,120,676 A | 9/2000 | Heller et al. | |
| 6,121,009 A | 9/2000 | Heller et al. | |
| 6,134,461 A | 10/2000 | Say et al. | |
| 6,143,164 A | 11/2000 | Heller et al. | |
| 6,162,611 A | 12/2000 | Heller et al. | |
| 6,175,752 B1 | 1/2001 | Say et al. | |
| 6,183,412 B1 | 2/2001 | Benkowski et al. | |
| 6,246,992 B1 | 6/2001 | Brown | |
| 6,259,937 B1 | 7/2001 | Schulman et al. | |
| 6,329,161 B1 | 12/2001 | Heller et al. | |
| 6,408,330 B1 | 6/2002 | DeLaHuerga | |
| 6,424,847 B1 | 7/2002 | Mastrototaro et al. | |
| 6,472,122 B1 | 10/2002 | Schulman et al. | |
| 6,484,045 B1 | 11/2002 | Holker et al. | |
| 6,484,046 B1 | 11/2002 | Say et al. | |
| 6,485,465 B2 | 11/2002 | Moberg et al. | |
| 6,503,381 B1 | 1/2003 | Gotoh et al. | |
| 6,511,439 B1 * | 1/2003 | Tabata | A61B 5/15003 600/573 |
| 6,514,718 B2 | 2/2003 | Heller et al. | |
| 6,544,173 B2 | 4/2003 | West et al. | |
| 6,553,263 B1 | 4/2003 | Meadows et al. | |
| 6,554,798 B1 | 4/2003 | Mann et al. | |
| 6,558,320 B1 | 5/2003 | Causey, III et al. | |
| 6,558,351 B1 | 5/2003 | Steil et al. | |

(56) References Cited

U.S. PATENT DOCUMENTS

| | | |
|---|---|---|
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,746,582 B2 | 6/2004 | Heller et al. |
| 6,747,556 B2 | 6/2004 | Medema et al. |
| 6,749,740 B2 | 6/2004 | Liamos et al. |
| 6,752,787 B1 | 6/2004 | Causey, III et al. |
| 6,809,653 B1 | 10/2004 | Mann et al. |
| 6,817,990 B2 | 11/2004 | Yap et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,153,263 B2 | 12/2006 | Carter et al. |
| 7,153,289 B2 | 12/2006 | Vasko |
| 7,396,330 B2 | 7/2008 | Banet et al. |
| 7,621,893 B2 | 11/2009 | Moberg et al. |
| 7,828,764 B2 | 11/2010 | Moberg et al. |
| 7,905,868 B2 | 3/2011 | Moberg et al. |
| 2001/0044731 A1 | 11/2001 | Coffman et al. |
| 2002/0013518 A1 | 1/2002 | West et al. |
| 2002/0055857 A1 | 5/2002 | Mault et al. |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey, III et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0133166 A1 | 7/2004 | Moberg et al. |
| 2004/0167465 A1 | 8/2004 | Mihai et al. |
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0154271 A1 | 7/2005 | Rasdal et al. |
| 2005/0192557 A1 | 9/2005 | Brauker et al. |
| 2005/0197626 A1* | 9/2005 | Moberg ............ A61M 5/14566 604/131 |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088521 A1 | 4/2007 | Shmueli et al. |
| 2007/0135866 A1 | 6/2007 | Baker et al. |
| 2008/0132843 A1* | 6/2008 | Sharifi ............... A61M 5/1458 604/151 |
| 2008/0154503 A1 | 6/2008 | Wittenber et al. |
| 2008/0269687 A1 | 10/2008 | Chong et al. |
| 2009/0081951 A1 | 3/2009 | Erdmann et al. |
| 2009/0082635 A1 | 3/2009 | Baldus et al. |
| 2009/0299290 A1 | 12/2009 | Moberg |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |

OTHER PUBLICATIONS (Animas Corporation, 1999). Animas . . . bringing new life to insulin therapy.
Bode B W, et al. (1996). Reduction in Severe Hypoglycemia with Long-Term Continuous Subcutaneous Insulin Infusion in Type I Diabetes. Diabetes Care, vol. 19, No. 4, 324-327.
Boland E (1998). Teens Pumping it Up! Insulin Pump Therapy Guide for Adolescents. 2nd Edition.
Brackenridge B P (1992). Carbohydrate Gram Counting A Key to Accurate Mealtime Boluses in Intensive Diabetes Therapy. Practical Diabetology, vol. 11, No. 2, pp. 22-28.
Brackenridge, B P et al. (1995). Counting Carbohydrates How to Zero in on Good Control. MiniMed Technologies Inc.
Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.
Hirsch I B et al. (1990). Intensive Insulin Therapy for Treatment of Type I Diabetes. Diabetes Care, vol. 13, No. 12, pp. 1265-1283.
Kulkarni K et al. (1999). Carbohydrate Counting a Primer for Insulin Pump Users to Zero in on Good Control. MiniMed Inc.
Marcus A O et al. (1996). Insulin Pump Therapy Acceptable Alternative to Injection Therapy. Postgraduate Medicine, vol. 99, No. 3, pp. 125-142.
Reed J et al. (1996). Voice of the Diabetic, vol. 11, No. 3, pp. 1-38.
Skyler J S (1989). Continuous Subcutaneous Insulin Infusion [CSII] With External Devices: Current Status. Update in Drug Delivery Systems, Chapter 13, pp. 163-183. Future Publishing Company.
Skyler J S et al. (1995). The Insulin Pump Therapy Book Insights from the Experts. MiniMed•Technologies.
Strowig S M (1993). Initiation and Management of Insulin Pump Therapy. The Diabetes Educator, vol. 19, No. 1, pp. 50-60.

(56) References Cited

OTHER PUBLICATIONS

Walsh J, et al. (1989). Pumping Insulin: The Art of Using an Insulin Pump. Published by MiniMed•Technologies.
(Intensive Diabetes Management, 1995). Insulin Infusion Pump Therapy. pp. 66-78.
Disetronic My Choice™ D-TRON™ Insulin Pump Reference Manual. (no date).
Disetronic H-TRON® plus Quick Start Manual. (no date).
Disetronic My Choice H-TRONplus Insulin Pump Reference Manual. (no date).
Disetronic H-TRON®plus Reference Manual. (no date).
(MiniMed, 1996). The MiniMed 506. 7 pages. Retrieved on Sep. 16, 2003 from the World Wide Web: http://web.archive.org/web/19961111054527/www.minimed.com/files/506_pic.htm.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump A Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.

Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.
Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.
Nakamoto, S., et al., "A Lift-Off Method for Patterning Enzyme-Immobilized Membranes in Multi-Biosensors," Sensors and Actuators 13, 1988, pp. 165-172.
Nishida, Kenro, et al., "Clinical applications of teh wearable artifical endocrine pancreas with the newly designed needle-type glucose sensor," Elsevier Sciences B.V., 1994, pp. 353-358.
Nishida, Kenro, et al., "Development of a ferrocene-mediated needle-type glucose sensor covereed with newly designd biocompatible membrane, 2-methacryloyloxyethylphosphorylcholine-co-n-butyl nethacrylate," Medical Progress Through Technology, vol. 21, 1995, pp. 91-103.
Poitout, V., et al., "A glucose monitoring system for on line estimation oin man of blood glucose concentration using a minia-

(56) References Cited

OTHER PUBLICATIONS turized glucose sensor implanted in the subcutaneous tissue adn a wearable control unit," Diabetologia, vol. 36, 1991, pp. 658-663.

Reach, G., "A Method for Evaluating in vivo the Functional Characteristics of Glucose Sensors," Biosensors 2, 1986, pp. 211-220.

Shaw, G. W., et al., "In vitro testing of a simply constructed, highly stable glucose sensor suitable for implantation in diabetic patients," Biosensors & Bioelectronics 6, 1991, pp. 401-406.

Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.

Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.

Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.

Shichiri, Motoaki, et al., "Glycaemic Control in a Pacreatectomized Dogs with a Wearable Artificial Endocrine Pancreas," Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.

Shichiri, M., et al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

\* cited by examiner

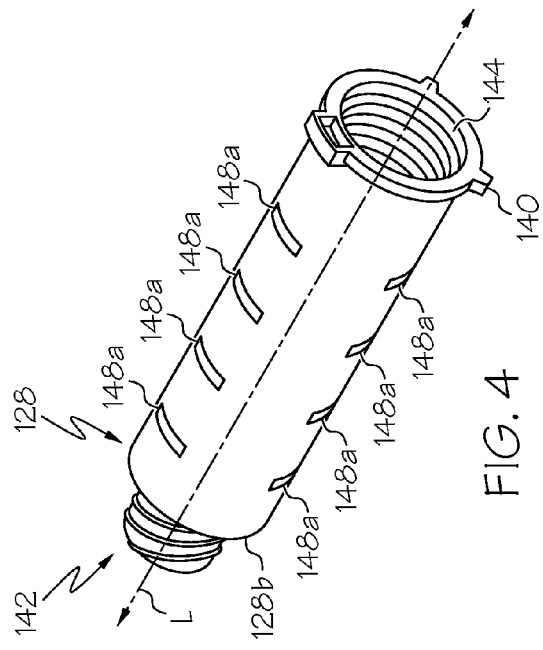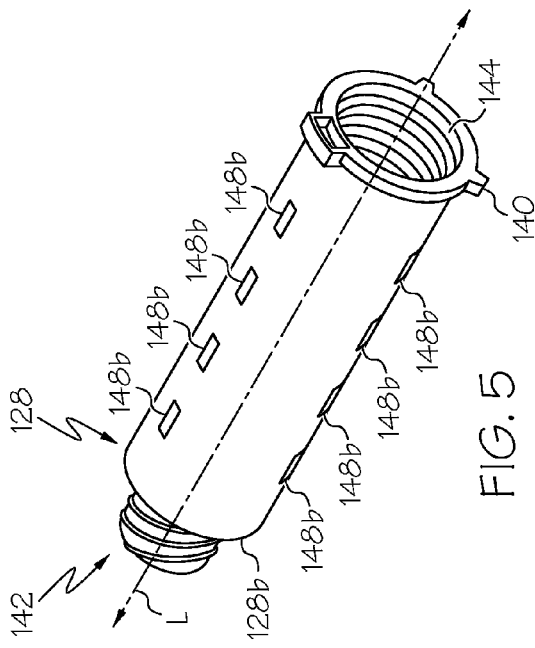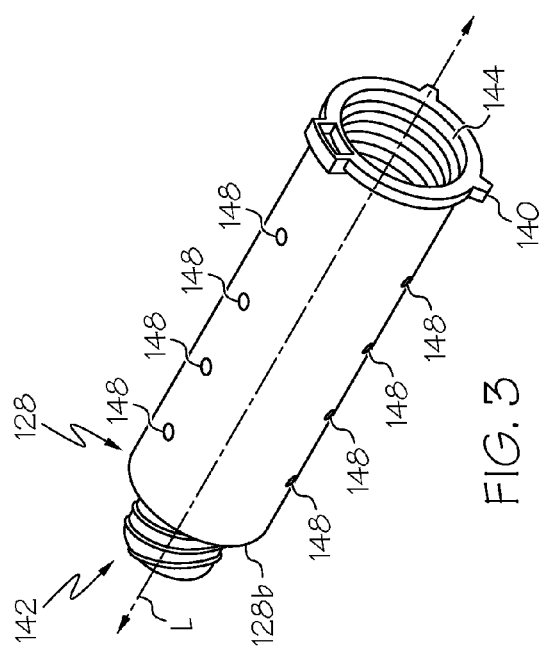

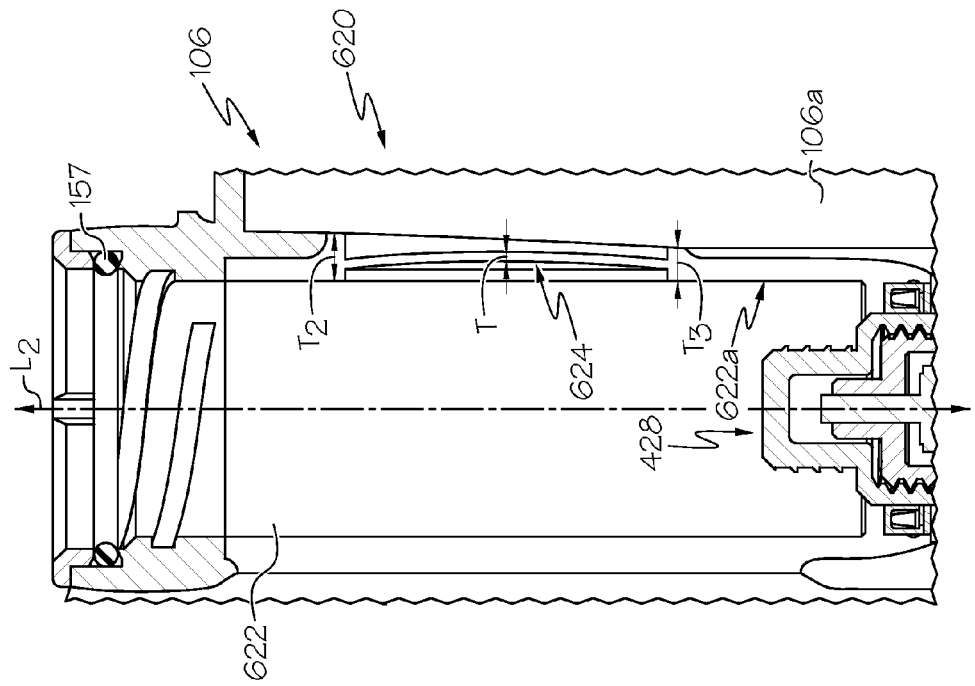
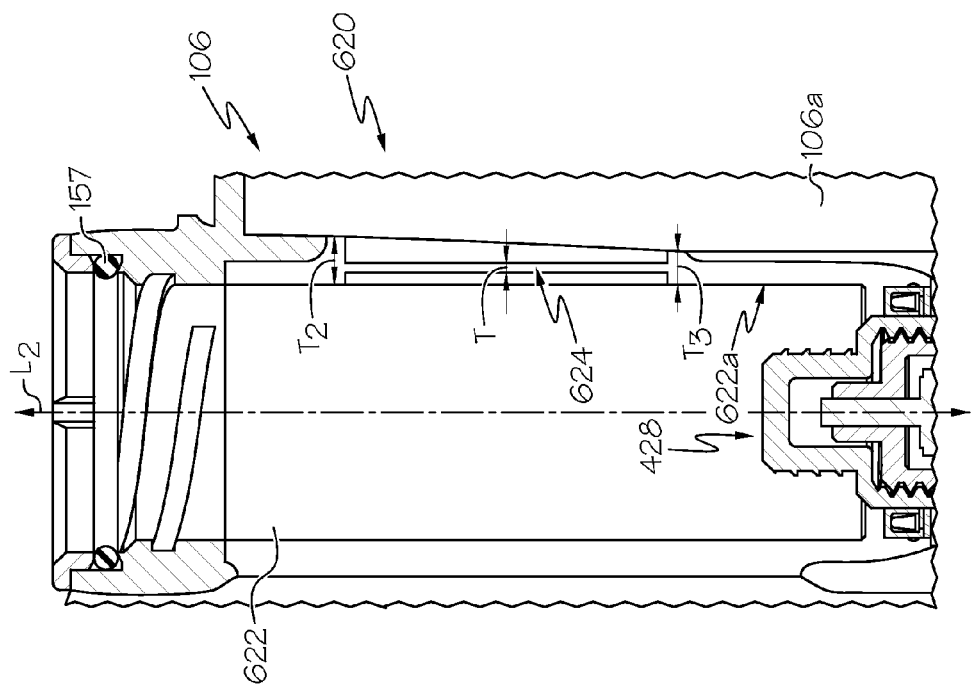

SYSTEMS FOR MANAGING RESERVOIR CHAMBER PRESSURE

TECHNICAL FIELD

Embodiments of the subject matter described herein relate generally to fluid infusion devices for delivering a medication fluid to the body of a user. More particularly, embodiments of the subject matter relate to systems for managing pressure in a fluid reservoir chamber of a fluid infusion device.

BACKGROUND

Certain diseases or conditions may be treated, according to modern medical techniques, by delivering a medication or other substance to the body of a user, either in a continuous manner or at particular times or time intervals within an overall time period. For example, diabetes is commonly treated by delivering defined amounts of insulin to the user at appropriate times. Some common modes of providing insulin therapy to a user include delivery of insulin through manually operated syringes and insulin pens. Other modern systems employ programmable fluid infusion devices (e.g., insulin pumps) to deliver controlled amounts of insulin to a user.

A fluid infusion device suitable for use as an insulin pump may be realized as an external device or an implantable device, which is surgically implanted into the body of the user. External fluid infusion devices include devices designed for use in a generally stationary location (for example, in a hospital or clinic), and devices configured for ambulatory or portable use (to be carried by a user). External fluid infusion devices may establish a fluid flow path from a fluid reservoir to the patient via, for example, a suitable hollow tubing. Generally, in order to advance fluid from the fluid reservoir, a pressure is applied to the fluid to direct the fluid out of the reservoir and through the hollow tubing.

Accordingly, it is desirable to provide systems for managing pressure in a fluid reservoir chamber of a fluid infusion device. Furthermore, other desirable features and characteristics will become apparent from the subsequent detailed description and the appended claims, taken in conjunction with the accompanying drawings and the foregoing technical field and background.

BRIEF SUMMARY

In one embodiment, a fluid infusion device is provided. The fluid infusion device comprises a housing having a chamber for receiving a fluid reservoir. The fluid infusion device also comprises a drive system contained within the housing. A portion of the drive system is movable for dispensing fluid from the fluid reservoir. The fluid infusion device comprises a pressure management system at least partially defined in the portion of the drive system to vent air from the chamber.

According to one embodiment, a fluid infusion device is also provided. The fluid infusion device comprises a housing having a chamber and a fluid reservoir contained within the chamber of the housing. The fluid infusion device also comprises a connector body coupled to the housing and the fluid reservoir to define a fluid flow path out of the housing. The connector body includes one or more vents to vent air from the chamber. The fluid infusion device comprises a drive system contained within the housing and coupled to the fluid reservoir. The drive system includes a slide movable relative to the fluid reservoir to dispense fluid from the fluid reservoir. The fluid infusion device further comprises a pressure management system at least partially defined in the portion of the drive system to vent air from the chamber.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

FIG. 3 is a perspective view of a portion of a drive system of the fluid infusion device of FIG. 1 according to an exemplary embodiment;

FIG. 4 is a perspective view of a portion of a drive system of the fluid infusion device of FIG. 1 according to an exemplary embodiment;

FIG. 5 is a perspective view of a portion of a drive system of the fluid infusion device of FIG. 1 according to an exemplary embodiment;

FIG. 13 is a schematic cross-sectional view of an exemplary pressure management system for use with the fluid infusion device of FIG. 1, in which the pressure management system is in a first position;

FIG. 14 is a schematic cross-sectional view of an exemplary pressure management system for use with the fluid infusion device of FIG. 1, in which the pressure management system is in a second position;

DETAILED DESCRIPTION

Figure 1:
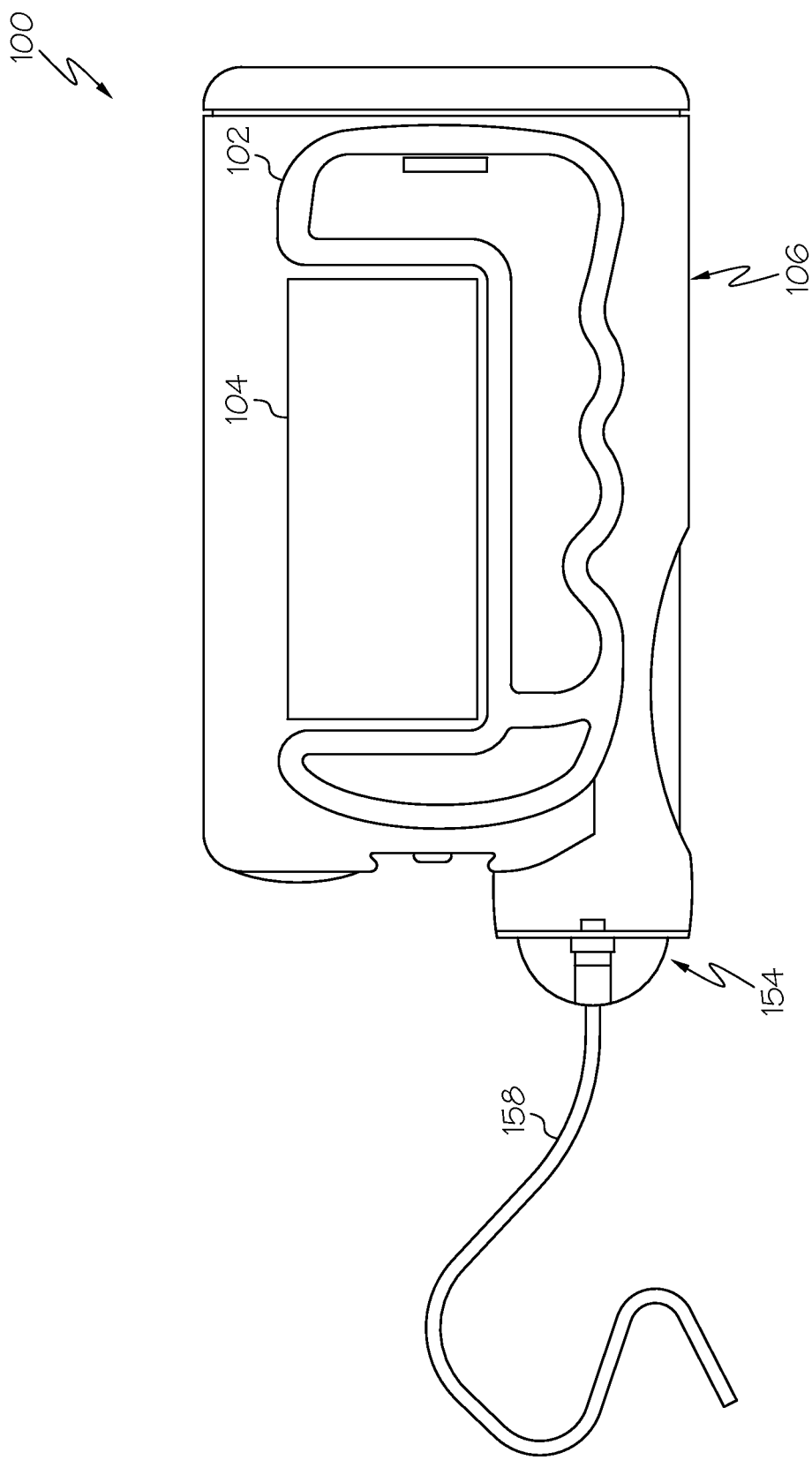
FIG. 1 is a perspective view of an exemplary embodiment of a fluid infusion device according to various teachings of the present disclosure.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may be used in the following description for the purpose of reference only, and thus are not intended to be limiting. For example, terms such as "top", "bottom", "upper", "lower", "above", and "below" could be used to refer to directions in the drawings to which reference is made. Terms such as "front", "back", "rear", "side", "outboard", and "inboard" could be used to describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

The following description relates to a fluid infusion device of the type used to treat a medical condition of a user. The infusion device can be used for infusing fluid into the body of a user. The non-limiting examples described below relate to a medical device used to treat diabetes (more specifically, an insulin pump), although embodiments of the disclosed subject matter are not so limited. Accordingly, the infused medication fluid is insulin in certain embodiments. In alternative embodiments, however, many other fluids may be administered through infusion such as, but not limited to, disease treatments, drugs to treat pulmonary hypertension, iron chelation drugs, pain medications, anti-cancer treatments, medications, vitamins, hormones, or the like. For the sake of brevity, conventional features and characteristics related to infusion system operation, insulin pump and/or infusion set operation, fluid reservoirs, and fluid syringes may not be described in detail here. Examples of infusion pumps and/or related pump drive systems used to administer insulin and other medications may be of the type described in, but not limited to: U.S. Patent Publication Nos. 2009/0299290 and 2008/0269687; U.S. Pat. Nos. 4,562,751; 4,678,408; 4,685,903; 5,080,653; 5,505,709; 5,097,122; 6,485,465; 6,554,798; 6,558,351; 6,659,980; 6,752,787; 6,817,990; 6,932,584; 7,621,893; 7,828,764; and 7,905,868; which are each incorporated by reference herein.

Figure 1A:
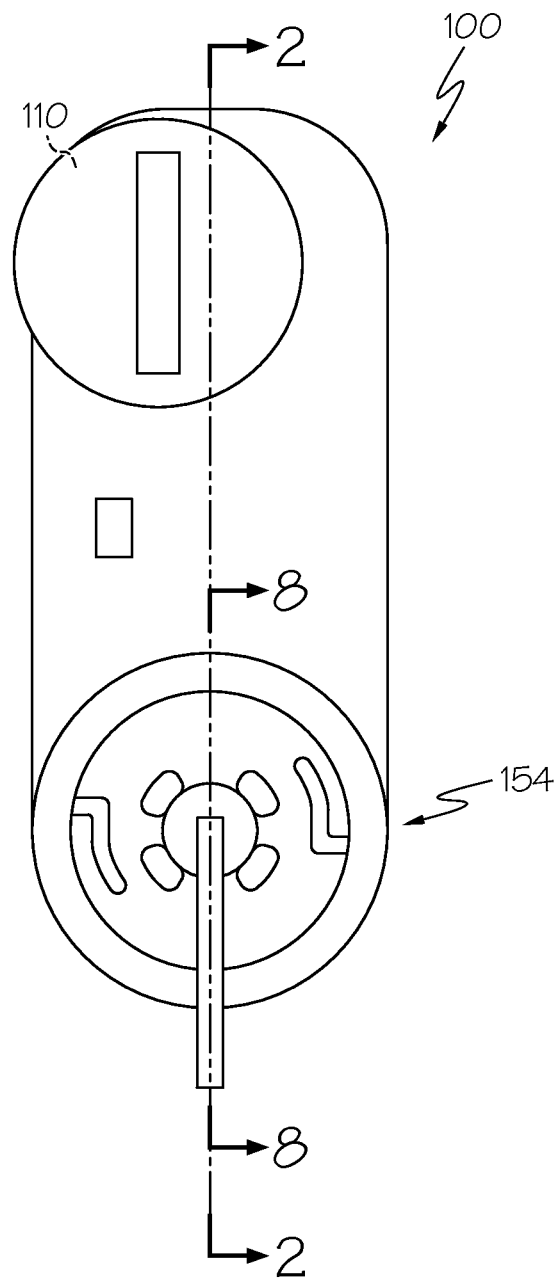
FIG. 1A is a top view of the fluid infusion device of FIG. 1.

FIG. 1 is a perspective view of an exemplary embodiment of a fluid infusion device 100, and FIG. 1A is a top view of the fluid infusion device 100. The fluid infusion device 100 is designed to be carried or worn by the patient. The fluid infusion device 100 may leverage a number of conventional features, components, elements, and characteristics of existing fluid infusion devices. For example, the fluid infusion device 100 may incorporate some of the features, components, elements, and/or characteristics described in U.S. Pat. Nos. 6,485,465 and 7,621,893, the relevant content of which is incorporated by reference herein.

With reference to FIG. 1, the fluid infusion device 100 includes a user interface 102 and a display 104 coupled to a housing 106. The user interface 102 includes one or more user input devices, such as buttons, which can be activated by the user. The user interface 102 can be used to administer a bolus of insulin, to change therapy settings, to change user preferences, to select display features, and the like. Although not required, the illustrated embodiment of the fluid infusion device 100 includes the display 104. The display 104 can be used to present various types of information or data to the user, such as, without limitation: the current glucose level of the patient; the time; a graph or chart of the patient's glucose level versus time; device status indicators; etc. In some embodiments, the display 104 is realized as a touch screen display element and, therefore, the display 104 also serves as a user interface component.

Figure 2:
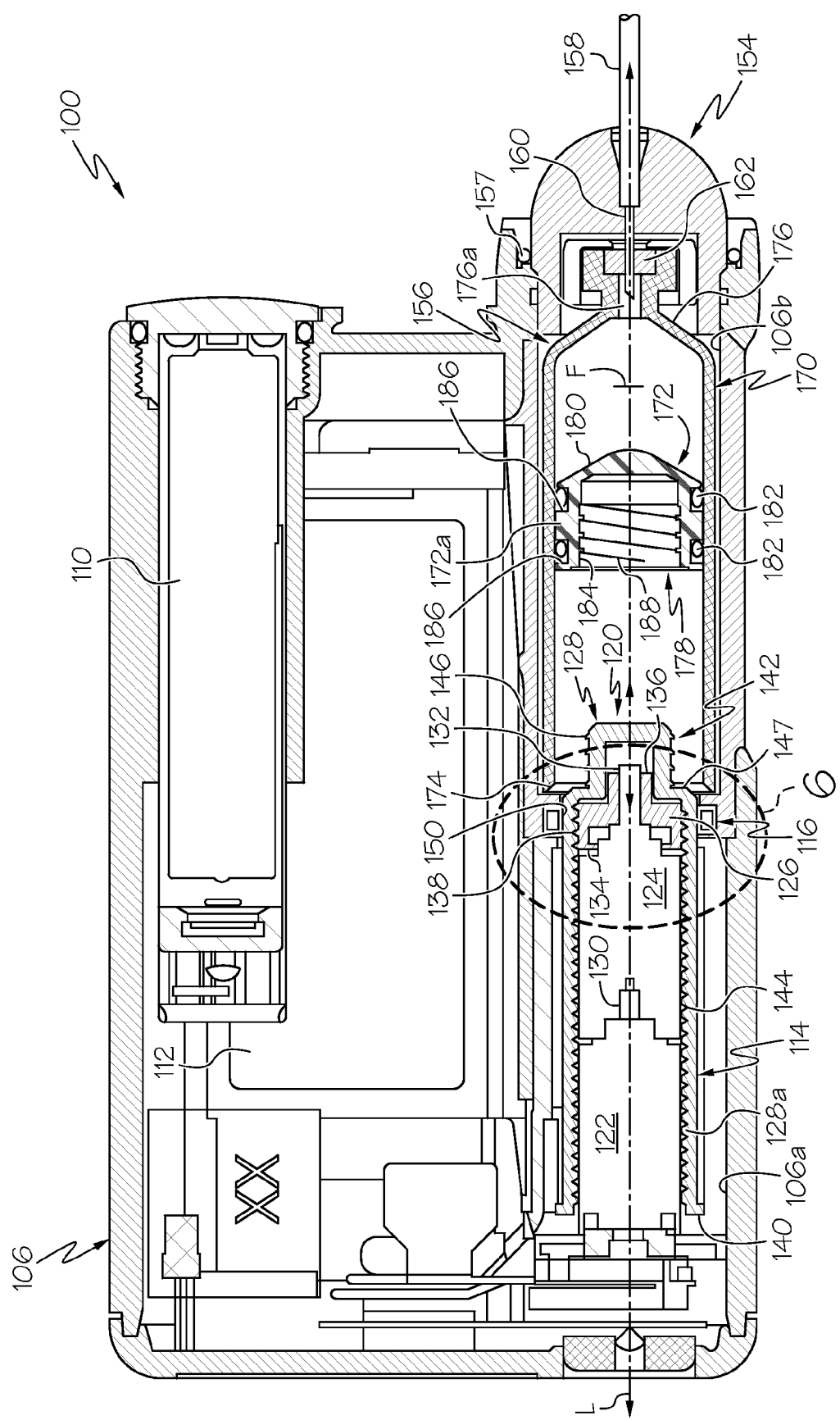
FIG. 2 is cross-sectional view of the fluid infusion device of FIG. 1, taken along line 2-2 of FIG. 1A.

With reference to FIG. 2, the housing 106 of the fluid infusion device 100 accommodates a power supply 110, a controller 112, a drive system 114, a seal 116, a fluid reservoir system 118 and a secondary pressure management system 120. Generally, the power supply 110, the controller 112, the drive system 114 and the seal 116 are accommodated in a pump chamber 106a defined by the housing 106, and the fluid reservoir system 118 is accommodated in a reservoir chamber 106b defined by the housing 106. As will be discussed in greater detail herein, the pressure management system 120 enables air from within the reservoir chamber 106b to be vented into the pump chamber 106a of the housing 106. By venting the air within the reservoir chamber 106b into the pump chamber 106a of the housing 106, the pressure increases within the reservoir chamber 106b can be minimized, as will be discussed.

The power supply 110 is any suitable device for supplying the fluid infusion device 100 with power, including, but not limited to, a battery. In one example, the power supply 110 can be removable relative to the housing 106, however, the power supply 110 can be fixed within the housing 106. The controller 112 is in communication with the user interface 102, display 104, power supply 110 and drive system 114. The controller 112 controls the operation of the fluid infusion device 100 based on patient specific operating parameters. For example, the controller 112 controls the supply of power from the power supply 110 to the drive system 114 to activate the drive system 114 to dispense fluid from the fluid reservoir system 118. Further detail regarding the control of the fluid infusion device 100 can be found in U.S. Pat. Nos. 6,485,465 and 7,621,893, the relevant content of which was previously incorporated herein by reference.

The drive system 114 cooperates with the fluid reservoir system 118 to dispense the fluid from the fluid reservoir system 118. In one example, the drive system 114 includes a motor 122, a gear box 124, a drive screw 126 and a slide 128. The motor 122 receives power from the power supply 110. In one example, the motor 122 is an electric motor. The motor 122 includes an output shaft 130, which is coupled to the gear box 124. In one embodiment, the gear box 124 is a reduction gear box. The gear box 124 includes an output shaft 132, which is coupled to the drive screw 126.

The drive screw 126 includes a generally cylindrical distal portion 134 and a generally cylindrical proximal portion 136. The distal portion 134 has a diameter, which can be larger than a diameter of the proximal portion 136. The distal portion 134 includes a plurality of threads 138. The threads 138 are generally formed about an exterior circumference of the distal portion 134. The proximal portion 136 is generally unthreaded, and can be sized to be received within a portion of the slide 128. Thus, the proximal portion 136 can serve to align the drive screw 126 within the slide 128 during assembly, for example.

With continued reference to FIG. 2, the slide 128 is substantially cylindrical and includes a distal slide end 140, a proximal slide end 142 and a plurality of threads 144. The distal slide end 140 is adjacent to the motor 122 when the slide 128 is in a first, fully retracted position and the proximal slide end 142 is adjacent to the drive screw 126 when the slide 128 is in the first, fully retracted position. The proximal slide end 142 includes a projection 146 and a shoulder 147, which cooperate with the fluid reservoir system 118 to dispense the fluid from the fluid reservoir system 118. In one example, the projection 146 can have a diameter that is smaller than a diameter of a remainder of the slide 128. It should be noted that the use of the projection 146 is merely exemplary, as the slide 128 need not include a projection 146 such that the proximal slide end 142 can be flat or planar. The shoulder 147 is defined adjacent to the projection 146 and contacts a portion of the fluid reservoir system 118 to dispense fluid from the fluid reservoir system 118, as will be discussed in greater detail herein.

The plurality of threads 144 of the slide 128 are formed along an interior surface 128*a* of the slide 128 between the distal slide end 140 and the proximal slide end 142. Generally, the threads 144 do not extend into the projection 146 of the proximal slide end 142. The threads 144 are formed so as to threadably engage the threads 138 of the drive screw 126. Thus, the rotation of the drive screw 126 causes the linear translation of the slide 128.

In this regard, the slide 128 is generally sized such that in a first, retracted position, the motor 122, the gear box 124 and the drive screw 126 are substantially surrounded by the slide 128. The slide 128 is movable to a second, fully extended position through the operation of the motor 122. The slide 128 is also movable to a plurality of positions between the first, retracted position and the second, fully extended position via the operation of the motor 122. Generally, the operation of the motor 122 rotates the output shaft 130, which is coupled to the gear box 124. The gear box 124 reduces the torque output by the motor 122, and the output shaft 132 of the gear box 124 rotates the drive screw 126, which moves along the threads 144 formed within the slide 128. The movement or rotation of the drive screw 126 relative to the slide 128 causes the movement or linear translation of the slide 128 within the housing 106. The advancement of the slide 128 into a portion of the fluid reservoir system 118 causes the fluid reservoir system 118 to dispense fluid.

With reference to FIG. 3, the slide 128 also includes one or more air conduits 148, which are defined along an exterior surface 128*b* of the slide 128. Generally, the air conduits 148 are defined so as to be spaced apart along the exterior surface 128*b* from the distal slide end 140 to the proximal slide end 142 and to be spaced apart about a perimeter or circumference of the slide 128. Thus, the air conduits 148 generally extend along a longitudinal axis L of the slide 128. In the example of FIG. 3, the air conduits 148 comprise cylindrical depressions or dimples defined in the exterior surface 128*b*, however, the air conduits 148 can have any desired shape that facilitates air flow out of the fluid reservoir system 118 as will be discussed in greater detail herein. It should also be noted that although the air conduits 148 are illustrated herein as comprising discrete dimples defined in the exterior surface 128*b*, the air conduits 148 may be defined about the circumference of the slide 128 if desired. Further, while eight air conduits 148 are illustrated herein, it should be noted that the slide 128 can include any number of air conduits 148, including a single air conduit 148. In addition, it should be noted that the spacing and location of the air conduits 148 on the exterior surface 128*b* is merely exemplary, as the air conduits 148 may be defined in the exterior surface 128*b* at any desired location.

In one example, with reference to FIG. 4, the slide 128 includes one or more air conduits 148*a*, which are defined along an exterior surface 128*b* of the slide 128. In this example, the air conduits 148*a* are defined as horizontal slots having a greatest width in a direction perpendicular to the longitudinal axis L. The air conduits 148*a* are spaced apart along the exterior surface 128*b* of the slide 128 from the distal slide end 140 to the proximal slide end 142. It should also be noted that although the air conduits 148*a* are illustrated herein as comprising discrete slots defined in the exterior surface 128*b*, the air conduits 148*a* may be defined about the circumference of the slide 128 if desired. In addition, while eight air conduits 148*a* are illustrated herein, it should be noted that the slide 128 can include any number of air conduits 148*a*, including a single air conduit 148*a*. Further, it should be noted that the spacing and location of the air conduits 148*a* on the exterior surface 128*b* is merely exemplary, as the air conduits 148*a* may be defined in the exterior surface 128*b* at any desired location.

In one example, with reference to FIG. 5, the slide 128 includes one or more air conduits 148*b*, which are defined along an exterior surface 128*b* of the slide 128. In this example, the air conduits 148*b* are defined as vertical slots having a greatest width in a direction parallel to the longitudinal axis L. The air conduits 148*b* are spaced apart along the exterior surface 128*b* of the slide 128 from the distal slide end 140 to the proximal slide end 142. It should also be noted that although the air conduits 148*b* are illustrated herein as comprising discrete slots defined in the exterior surface 128*b*, the air conduits 148*b* may be defined about the circumference of the slide 128 if desired. In addition, while eight air conduits 148*b* are illustrated herein, it should be noted that the slide 128 can include any number of air conduits 148*b*, including a single air conduit 148*b*. Further, it should be noted that the spacing and location of the air conduits 148*b* on the exterior surface 128*b* is merely exemplary, as the air conduits 148*b* may be defined in the exterior surface 128*b* at any desired location.

Figure 6:
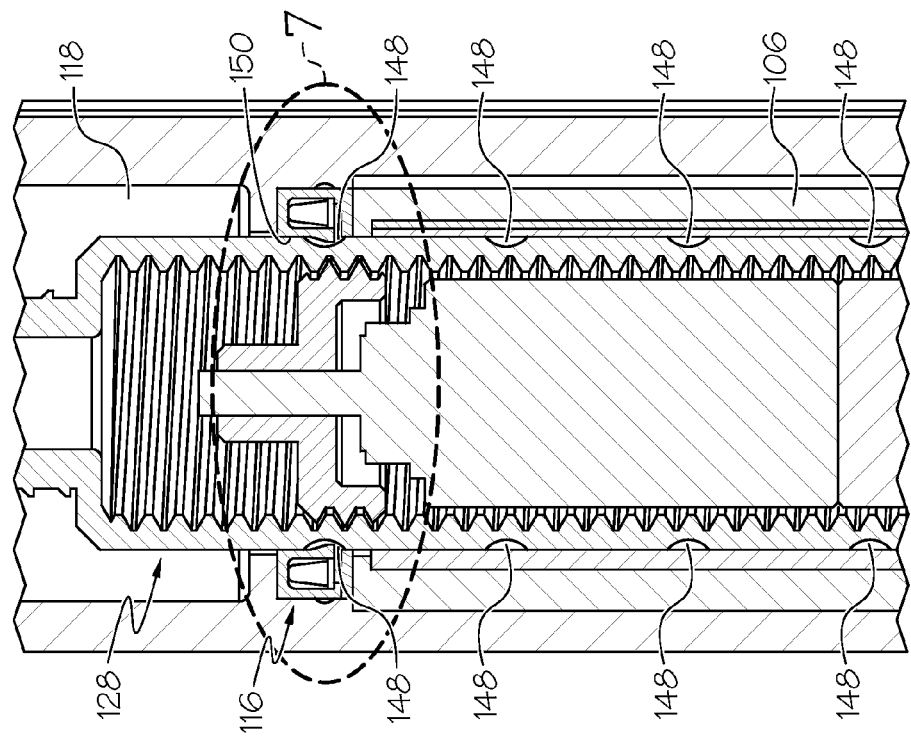
FIG. 6 is a detail view taken from FIG. 2 of an exemplary pressure management system for use with the fluid infusion device of FIG. 1.

With reference to FIG. 2, the seal 116 is disposed adjacent to the slide 128 and the reservoir chamber 106*b*. The seal 116 serves to separate the pump chamber 106*a* of the housing 106 from the reservoir chamber 106*b* to prevent the ingress of fluids to the motor 122, the gear box 124 and the drive screw 126 of the drive system 114. Generally, the seal 116 is positioned circumferentially about the slide 128 and defines an opening 150 through which the slide 128 can move. In one example, with reference to FIG. 6, the seal 116 cooperates with the slide 128 to define the pressure management system 120.

Figure 7:
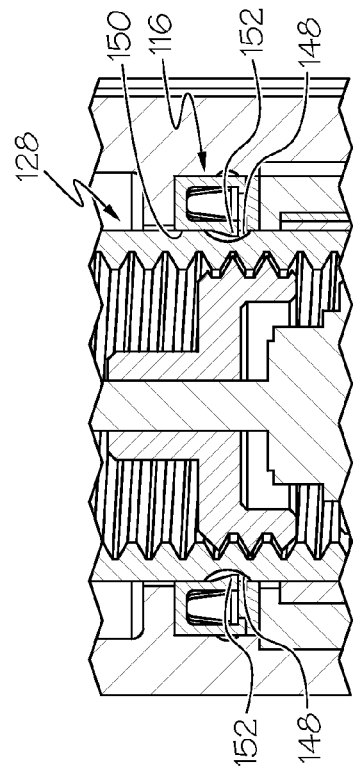
FIG. 7 is a detail view taken from FIG. 6 of the exemplary pressure management system for use with the fluid infusion device of FIG. 1.

In this regard, as the slide 128 moves relative to the seal 116 and advances into the fluid reservoir system 118, one or more of the air conduits 148 are exposed to enable air from the fluid reservoir system 118 to pass through the one or more air conduits 148 into the housing 106. In other words, with reference to FIG. 7, as the opening 150 of the seal 116 is generally sized to be substantially similar to the size of the circumference of the slide 128, and the air conduits 148 are formed as recesses within the exterior surface 128b of the slide 128, a gap or passage 152 is formed between the seal 116 and the slide 128 when the air conduit 148 is adjacent to the seal 116. Thus, the cooperation between the seal 116 and the air conduits 148 of the slide 128 serves to vent air from the reservoir chamber 106b, thereby managing or reducing pressure in the fluid reservoir system 118.

With reference back to FIG. 2, the fluid reservoir system 118 is shown. The fluid reservoir system 118 includes a reservoir cap or connector body 154 and a fluid reservoir 156. The connector body 154 creates a fluid path from the fluid reservoir 156 to the body of the patient. In one exemplary embodiment, the connector body 154 is removably coupled to the housing 106, through any suitable technique, such as threads, press-fitting, etc. Generally, the connector body 154 is suitably sized and configured to accommodate the replacement of fluid reservoirs 156 (which are typically disposable) as needed. A sealing member, such as an O-ring 157 may be coupled between the connector body 154 and the reservoir chamber 106b to prevent the ingress of fluids into the reservoir chamber 106b of the housing 106.

In one example, the connector body 154 accommodates the fluid path from the fluid reservoir 156 to a tube 158. The tube 158 represents the fluid flow path that couples the fluid reservoir 156 to an infusion unit that couples the tube 158 to the patient (not shown). In one example, the tube 158 is coupled to the fluid reservoir 156 via a connector needle 160, which is coupled to the connector body 154 and pierces a septum 162 associated with the fluid reservoir 156. It should be noted, however, that any suitable technique could be employed to create a fluid path from the fluid reservoir 156 to the patient, and thus, this embodiment is merely exemplary.

Figure 8:
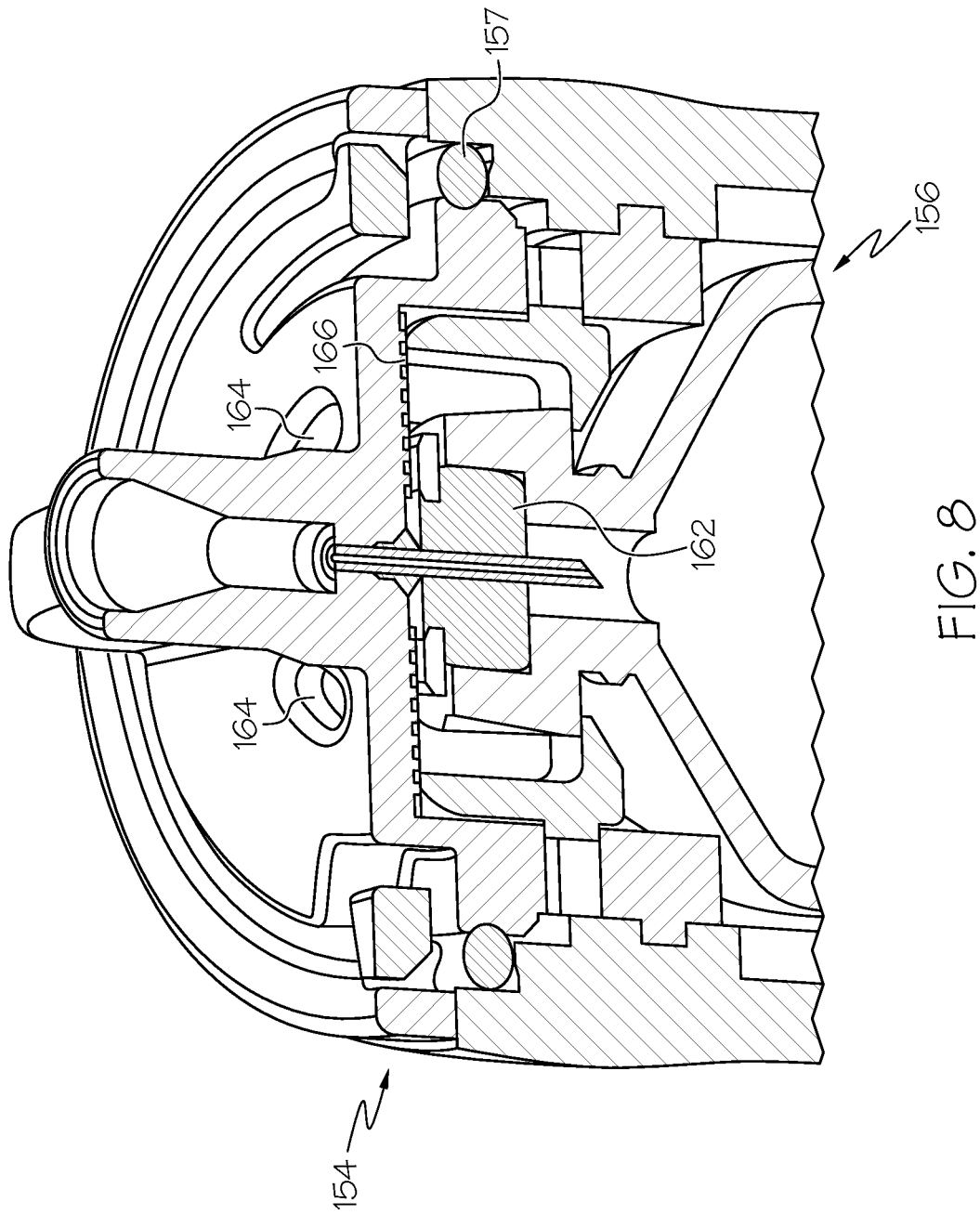
FIG. 8 is a detail cross-sectional view of an exemplary connector body of the fluid infusion device of FIG. 1, taken along line 8-8 of FIG. 1A.

With reference to FIG. 8, the connector body 154 may also include one or more vents 164 and a membrane 166. The one or more vents 164 also enable air to vent out of the reservoir chamber 106b. In this example, the one or more vents 164 enable air to vent into the environment. The one or more vents 164 act as a primary pressure management system for the fluid infusion device 100, and thus, the one or more vents 164 and the pressure management system 120 cooperate to manage pressure within the reservoir chamber 106b. The membrane 166 is generally a hydrophobic membrane, and allows air to pass through the vents 164 while preventing the ingress of fluids, such as water, into the fluid reservoir system 118.

With reference back to FIG. 2, the fluid reservoir 156 includes a body or barrel 170 and a stopper 172. The barrel 170 has a first or distal barrel end 174 and a second or proximal barrel end 176. Fluid F is retained within the barrel 170 between the distal barrel end 174 and the proximal barrel end 176. The distal barrel end 174 is positioned adjacent to the slide 128 when the fluid reservoir 156 is assembled in the housing 106. Generally, the distal barrel end 174 can have an open perimeter or can be circumferentially open such that the slide 128 is receivable within the barrel 170 through the distal barrel end 174. The proximal barrel end 176 defines a port 176a, which receives the connector needle 160 to define the fluid path. The proximal barrel end 176 can have any desirable size and shape configured to mate with at least a portion of the connector body 154.

The stopper 172 is disposed within the barrel 170. The stopper 172 is movable within and relative to the barrel 170 to dispense fluid from the fluid reservoir 156. When the barrel 170 is full of fluid, the stopper 172 is adjacent to the distal barrel end 174, and the stopper 172 is movable to a position adjacent to the proximal barrel end 176 to empty the fluid from the fluid reservoir 156. In one example, the stopper 172 is substantially cylindrical, and includes a distal stopper end 178, a proximal stopper end 180, at least one friction element 182 and a counterbore 184 defined from the distal stopper end 178 to the proximal stopper end 180.

The distal stopper end 178 is open about a perimeter of the distal stopper end 178, and thus, is generally circumferentially open. The proximal stopper end 180 is closed about a perimeter of the proximal stopper end 180 and is generally circumferentially closed. The proximal stopper end 180 includes a slightly conical external surface, however, the proximal stopper end 180 can be flat, convex, etc. The at least one friction element 182 is coupled to the stopper 172 about an exterior surface 172a of the stopper 172. In one example, the at least one friction element 182 comprises two friction elements, which include, but are not limited to, O-rings. The friction elements 182 are coupled to circumferential grooves 186 defined in the exterior surface 172a of the stopper 172.

The counterbore 184 receives the projection 146 of the slide 128 and the movement of the slide 128 causes the shoulder 147 of the slide 128 to contact and move the stopper 172. In one example, the counterbore 184 includes threads 188, however, the projection 146 of the slide 128 is not threadably engaged with the stopper 172. Thus, the threads 188 illustrated herein are merely exemplary.

With continued reference to FIG. 2, with the housing 106 assembled with the power supply 110, the controller 112 and the drive system 114, the fluid reservoir system 118 can be coupled to the housing 106. In one example, a full fluid reservoir 156 is inserted into the reservoir chamber 106b of the housing 106 such that the stopper 172 is adjacent to the projection 146 of the slide 128. As the drive screw 126 rotates, the slide 128 translates linearly. The advancement of the slide 128 decreases an available volume of the reservoir chamber 106b, which results in an increase in pressure in the reservoir chamber 106b.

As the pressure increases in the reservoir chamber 106b, in most instances, the pressure is relieved through the vents 164 of the connector body 154 (FIG. 8). In certain instances, for example, due to an obstruction of one or more of the vents 164, the pressure is relieved by the pressure management system 120. In this regard, as the slide 128 moves past the seal 116, the air conduits 148 enable pressure to be relieved by venting the air out of the reservoir chamber 106b into the pump chamber 106a of the housing 106 (FIG. 2). Thus, the pressure management system 120 manages the pressure within the reservoir chamber 106b by enabling the venting of air from the reservoir chamber 106b into the pump chamber 106a of the housing 106 through the air conduits 148.

Figure 9:
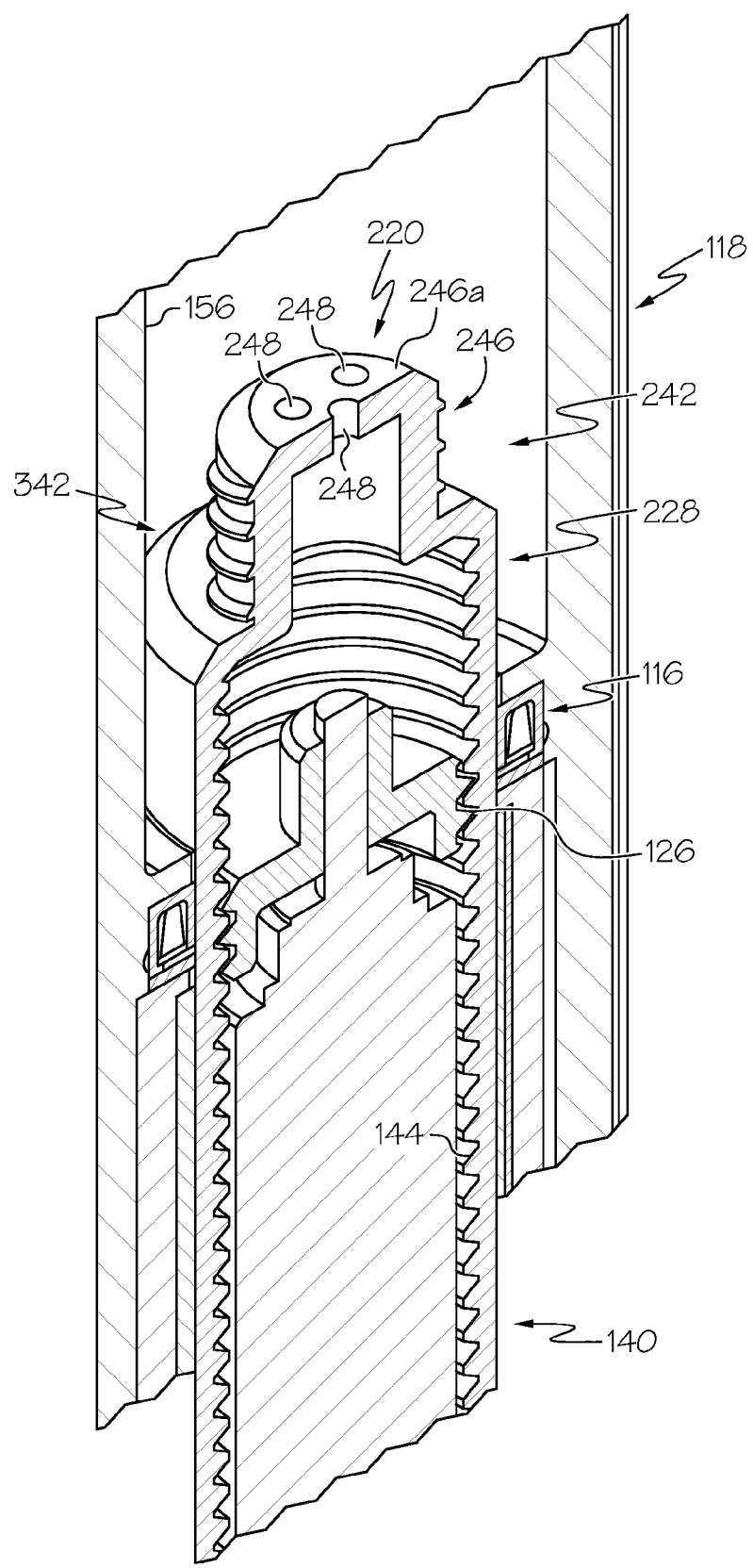
FIG. 9 is a schematic cross-sectional view of an exemplary pressure management system for use with the fluid infusion device of FIG. 1.

With reference now to FIG. 9, a pressure management system 220 is shown. As the pressure management system 220 can be used with the fluid infusion device 100 discussed with regard to FIGS. 1-8, only the pressure management system 220 will be discussed in detail herein.

In this example, the pressure management system 220 is defined in a slide 228 for use with the fluid infusion device 100. The slide 228 is substantially cylindrical and includes the distal slide end 140, a proximal slide end 242 and the plurality of threads 144. The proximal slide end 242 includes a projection 246, which cooperates with the fluid reservoir system 118 to dispense the fluid from the fluid reservoir system 118. In one example, the projection 246 can have a diameter that is smaller than a diameter of a remainder of the slide 228.

The pressure management system 220 is defined on the projection 246 of the slide 228. In one example, the pressure management system 220 comprises one or more bores 248, which are defined in and through an uppermost surface 246a of the projection 246. The bores 248 may be defined through the uppermost surface 246a in any desired pattern, and in one example, may be defined through the uppermost surface 246a so as to be spaced apart from or inward from an outer circumference of the uppermost surface 246a. In addition, it should be noted that while three bores 248 are illustrated herein, the pressure management system 220 can include any number of bores 248. The bores 248 can have any desired size or diameter, and the size or diameter may be varied amongst the bores 248 to enable tuning of the pressure management system 220 to the desired air flow rate. Moreover, while the bores 248 are illustrated herein as being cylindrical or with a circular perimeter, the bores 248 can have any desired polygonal shape, such as triangular or pentagonal, for example. It should be noted that the use of the projection 246 is merely exemplary, as the slide 228 need not include the projection 246 such that the proximal slide end 242 can be flat or planar, with the pressure management system 220 defined through the flat or planar end. Further, while the bores 248 are illustrated and described herein as being defined in the slide 228, the bores 248 may be defined at any desirable location to enable venting of the fluid reservoir 156, for example, the bores 248 may be defined in and through the seal 116. Thus, the location of the bores 248 is merely exemplary.

As discussed above, with the slide 228 assembled within the fluid infusion device 100, in order to dispense fluid from the fluid reservoir 156, the drive screw 126 rotates and the slide 228 translates linearly to move the stopper 172 (FIG. 2). The advancement of the slide 228 and the stopper 172 within the fluid reservoir 156 increases the pressure in the reservoir chamber 106b.

As the pressure increases in the reservoir chamber 106b, in most instances, the pressure is relieved through the vents 164 of the connector body 154 (FIG. 8). In certain instances, for example, due to an obstruction or one or more of the vents 164, the pressure is relieved by the pressure management system 220. In this regard, the bores 248 formed in the uppermost surface 246a of the slide 228 enable pressure to be relieved by venting the air out of the reservoir chamber 106b into the slide 228, and out of the slide 228 into the pump chamber 106a of the housing 106. Thus, the pressure management system 220 manages the pressure within the reservoir chamber 106b by enabling the venting of air from the reservoir chamber 106b through the bores 248 and into the pump chamber 106a of the housing 106.

Figure 10:
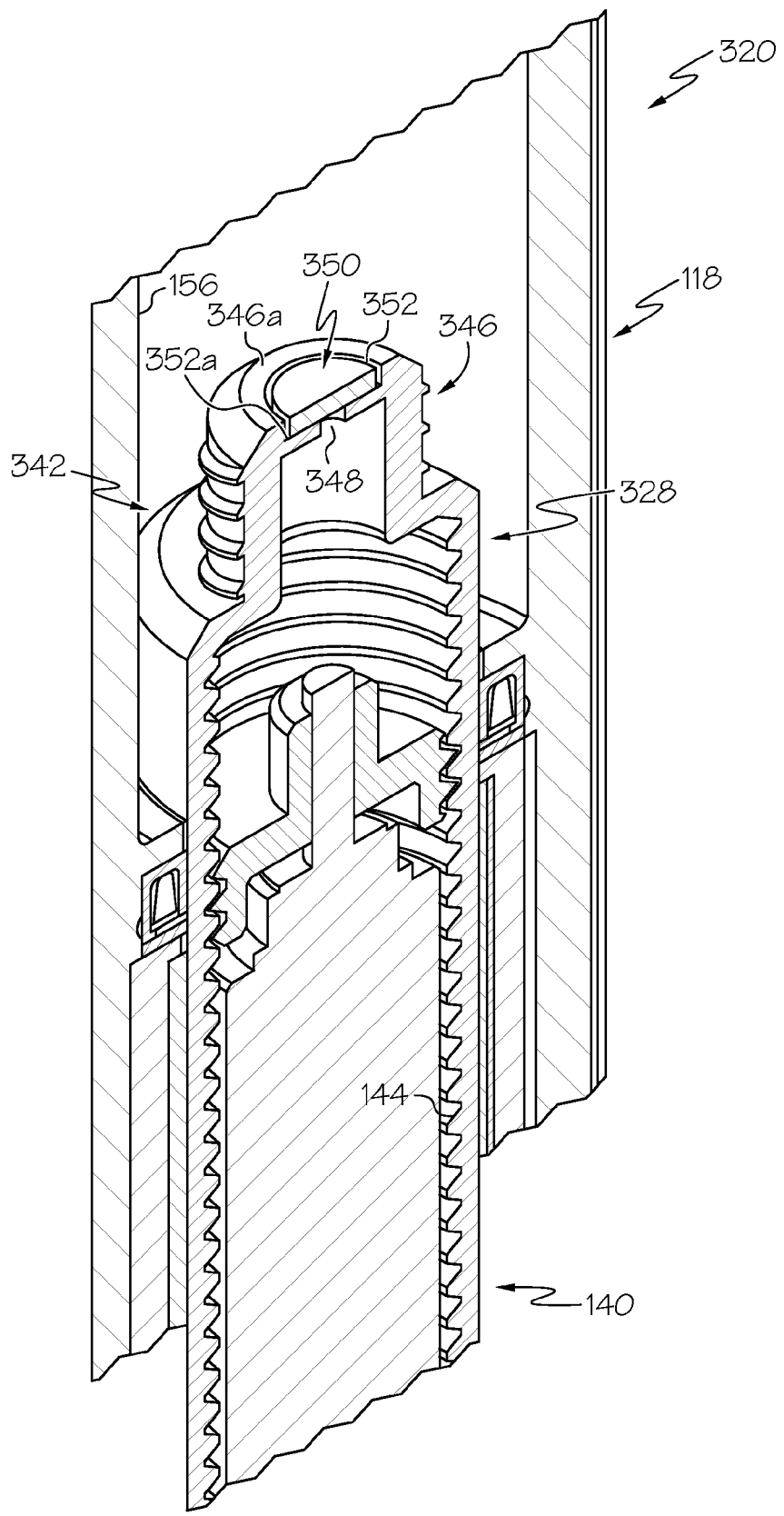
FIG. 10 is a schematic cross-sectional view of an exemplary pressure management system for use with the fluid infusion device of FIG. 1.

With reference to FIG. 10, a pressure management system 320 is shown. As the pressure management system 320 can be used with the fluid infusion device 100 discussed with regard to FIGS. 1-8, only the pressure management system 320 will be discussed in detail herein. Further, as the pressure management system 320 can be similar to the pressure management system 220 described with regard to FIG. 9, the same reference numerals will be employed to denote the same or similar components.

In this example, the pressure management system 320 is defined in a slide 328 for use with the fluid infusion device 100. The slide 328 is substantially cylindrical and includes the distal slide end 140, a proximal slide end 342 and the plurality of threads 144. The proximal slide end 342 includes a projection 346, which cooperates with the fluid reservoir system 118 to dispense the fluid from the fluid reservoir system 118. In one example, the projection 346 can have a diameter that is smaller than a diameter of a remainder of the slide 328.

The pressure management system 320 is defined on the projection 346 of the slide 328. In one example, the pressure management system 320 comprises one or more bores 348 and a membrane 350. In this example, the projection 346 includes an annular counterbore 352 defined in a proximal-most surface 346a. It should be noted that the use of the projection 346 is merely exemplary, as the slide 328 need not include the projection 346 such that the proximal slide end 342 can be flat or planar, with the annular counterbore 352 defined through the flat or planar end.

The bores 348 are defined in and through a surface 352a of the annular counterbore 352. The bores 348 may be defined through the surface 352a in any desired pattern, and in one example, may be defined through the surface 352a so as to be spaced apart from or inward from a perimeter or circumference of the annular counterbore 352. In addition, it should be noted that while a single bore 348 is illustrated herein, the pressure management system 320 can include any number of bores 348. The bore 348 can have any desired size or diameter, and the size or diameter may be varied to enable tuning of the pressure management system 320 to the desired air flow rate. Moreover, while the bore 348 is illustrated herein as being cylindrical or with a circular perimeter, the bore 348 can have any desired polygonal shape, such as triangular or pentagonal, for example.

The membrane 350 is coupled to the annular counterbore 352. In one example, the membrane 350 is coupled to the annular counterbore 352 so as to substantially cover the surface 352a, and thus, the one or more bores 348. The membrane 350 is coupled to the annular counterbore 352 through any suitable technique, including, but not limited to, ultrasonic welding of the membrane 350 to the surface 352a. Generally, the membrane 350 is hydrophobic, such that air may pass through the membrane, but fluid, such as water, does not.

With the slide 328 assembled within the fluid infusion device 100, in order to dispense fluid from the fluid reservoir 156, the drive screw 126 rotates, the slide 328 translates linearly. The advancement of the slide 328 decreases the volume of the reservoir chamber 106b, which may result in an increase in the pressure in the reservoir chamber 106b. As the pressure increases in the reservoir chamber 106b, in most instances, the pressure is relieved through the vents 164 of the connector body 154 (FIG. 8). In certain instances, the pressure is relieved by the pressure management system 320. In this regard, the bore 348 formed in the surface 352a of the slide 328 enables pressure to be relieved by venting the air out of the reservoir chamber 106b into the slide 328, and out of the slide 328 into the pump chamber 106a of the housing 106. The membrane 350 enables the air to pass through the bore 348, but prevents the passage of fluid, such as water, through the bore 348. Thus, the pressure management system 320 manages the pressure within the reservoir chamber 106b by enabling the venting of air from the reservoir chamber 106b through the bore 348, while preventing the ingress of fluid, such as water, through the bore 348.

Figure 11:
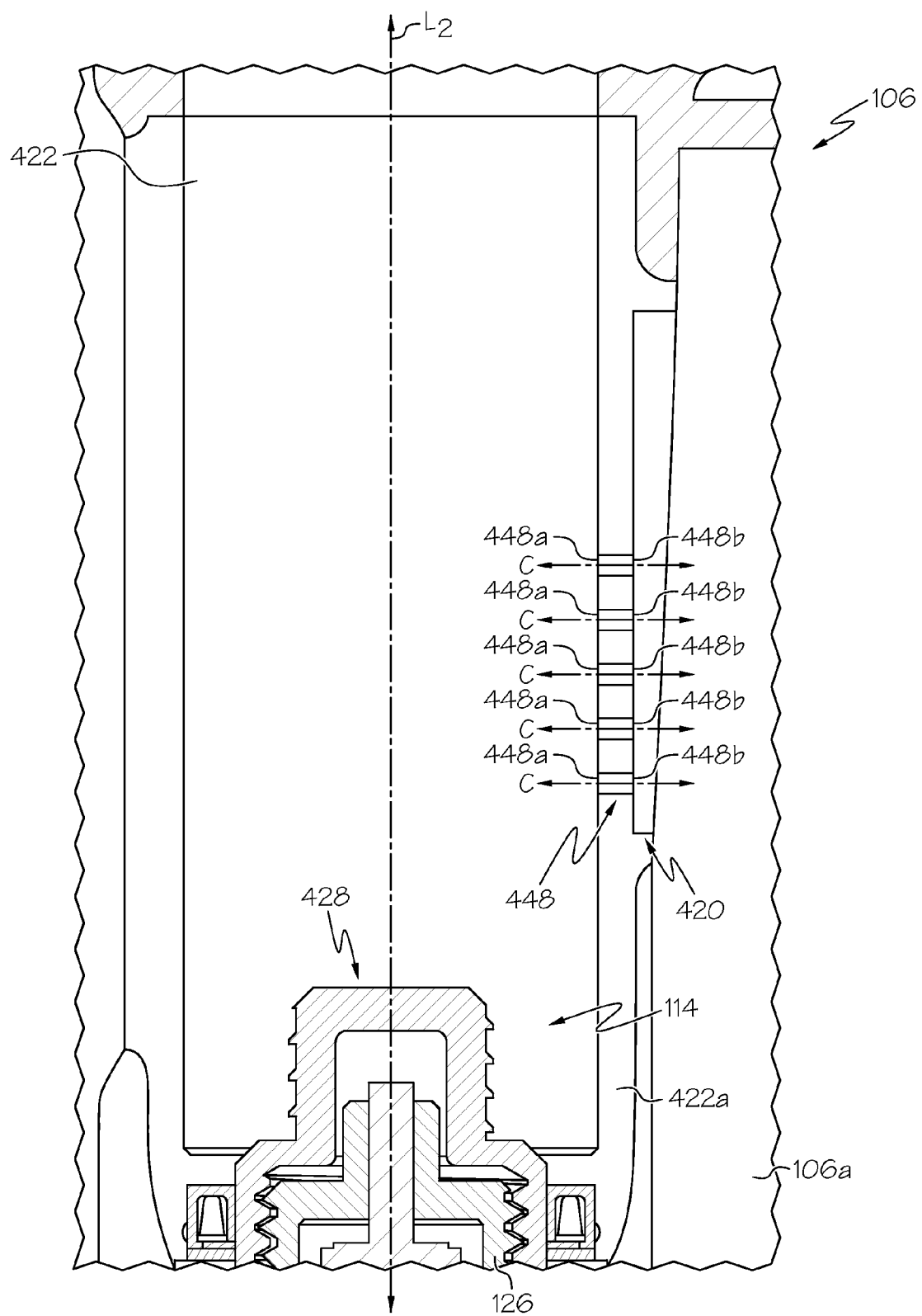
FIG. 11 is a schematic cross-sectional view of an exemplary pressure management system for use with the fluid infusion device of FIG. 1.

With reference now to FIG. 11, a pressure management system 420 is shown. As the pressure management system 420 can be used with the fluid infusion device 100 discussed with regard to FIGS. 1-8, only the pressure management system 420 will be discussed in detail herein.

In this example, the pressure management system 420 is defined in a portion of the housing 106 of the fluid infusion device 100. For example, the pressure management system 420 is defined in a reservoir chamber 422 of the housing 106 that receives the fluid reservoir 156 of the fluid reservoir system 118 (FIG. 2). The pressure management system 420 comprises one or more bores 448, which are defined in and through a wall 422a of the reservoir chamber 422 of the housing 106. The bores 448 may be defined through the wall 422a in any desired pattern, and in one example, may be defined through the wall 422a of the reservoir chamber 422 such that a centerline C of each bore 448 is substantially parallel to a longitudinal axis L2 of the reservoir chamber 422. The bores 448 may be arranged such that the bores 448 extend along the longitudinal axis L2 of the reservoir chamber 422, however, it should be noted that this arrangement of bores 448 is merely exemplary, as the bores 448 may be arranged offset from each other. A first end 448a of each of the bores 448 is in communication with the reservoir chamber 422. An opposite, second end 448b of each of the bores 448 is in communication with the pump chamber 106a of the housing 106 to vent the air from the bores 448 into the pump chamber 106a of the housing 106.

In addition, it should be noted that while five bores 448 are illustrated herein, the pressure management system 420 can include any number of bores 448. The bores 448 can have any desired size or diameter, and the size or diameter may be varied amongst the bores 448 to enable tuning of the pressure management system 420 to the desired air flow rate. Moreover, while the bores 448 are illustrated herein as being cylindrical or with a circular perimeter, the bores 448 can have any desired polygonal shape, such as triangular or pentagonal, for example. Further, while the bores 448 are illustrated and described herein as being defined in the wall 422a, the bores 448 may be defined at any desirable location to within the reservoir chamber 422 to enable venting of the reservoir chamber 422. Thus, the location of the bores 448 is merely exemplary.

With the fluid reservoir 156 received in the reservoir chamber 422, as the drive screw 126 rotates, a slide 428 translates linearly. As the slide 428 can be substantially similar to the slide 128 but without the one or more air conduits 148, the slide 428 will not be discussed in great detail herein. The advancement of the slide 428 decreases the volume of the reservoir chamber 422, which may result in an increase in the pressure in the reservoir chamber 422. As the pressure increases in the reservoir chamber 422, in most instances, the pressure is relieved through the vents 164 of the connector body 154 (FIG. 8). In certain instances, the pressure is relieved by the pressure management system 420. In this regard, the bores 448 formed in the wall 422a of the reservoir chamber 422 of the housing 106 enable pressure to be relieved by venting the air out of the reservoir chamber 422 into the pump chamber 106a of the housing 106. Thus, the pressure management system 420 manages the pressure within the reservoir chamber 422 by enabling the venting of air from the reservoir chamber 422 through the bores 448 and into the pump chamber 106a of the housing 106.

Figure 12:
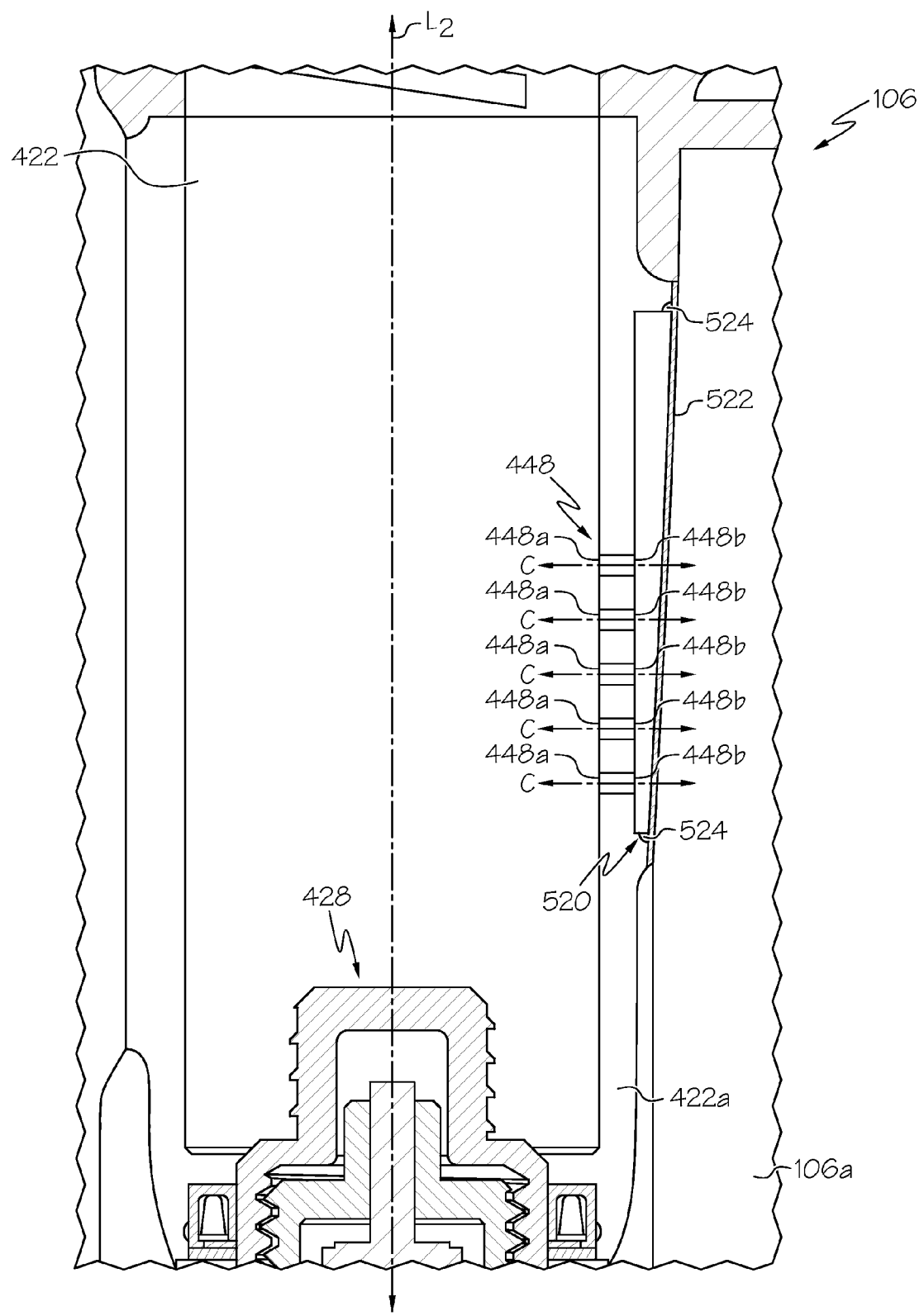
FIG. 12 is a schematic cross-sectional view of an exemplary pressure management system for use with the fluid infusion device of FIG. 1.

With reference to FIG. 12, a pressure management system 520 is shown. As the pressure management system 520 can be used with the fluid infusion device 100 discussed with regard to FIGS. 1-8, only the pressure management system 520 will be discussed in detail herein. Further, as the pressure management system 520 can be similar to the pressure management system 420 described with regard to FIG. 11, the same reference numerals will be employed to denote the same or similar components.

In the example of FIG. 12, the pressure management system 520 is defined in a portion of the housing 106 of the fluid infusion device 100. For example, the pressure management system 520 is defined in the reservoir chamber 422 of the housing 106 that receives the fluid reservoir 156 of the fluid reservoir system 118 (FIG. 2). The pressure management system 520 comprises the one or more bores 448, which are defined in and through the wall 422a of the reservoir chamber 422 of the housing 106 and a membrane 522. The bores 448 are in communication with the reservoir chamber 422 and the pump chamber 106a of the housing 106. Thus, the bores 448 enable air to be vented out of the reservoir chamber 422 through the bores 448 and into the pump chamber 106a of the housing 106 external from the reservoir chamber 422.

The membrane 522 is coupled to the wall 422a of the reservoir chamber 422. In one example, the membrane 522 is coupled to the wall 422a so as to substantially cover the bores 448. Thus, the membrane 522 in this example is coupled to the wall 422a on a side of the wall substantially opposite a side of the wall in contact with the fluid reservoir 156. The membrane 522 is coupled to the wall 422a through any suitable technique, including, but not limited to, ultrasonic welding. In the example of ultrasonic welding, a weld 524 extends between the membrane 522 and the wall 422a about a perimeter of the membrane 522. Generally, the membrane 522 is hydrophobic, such that air may pass through the membrane, but fluid, such as water, does not.

With the fluid reservoir 156 received in the reservoir chamber 422, as the drive screw 126 rotates, the slide 428 translates linearly. The advancement of the slide 428 decreases the volume of the reservoir chamber 422, which may result in an increase in the pressure in the reservoir chamber 422. As the pressure increases in the reservoir chamber 422, in most instances, the pressure is relieved through the vents 164 of the connector body 154 (FIG. 8). In certain instances, the pressure is relieved by the pressure management system 520. In this regard, the bores 448 formed in the wall 422a of the reservoir chamber 422 of the housing 106 enable pressure to be relieved by venting the air out of the reservoir chamber 422, through the bores 448, and into the pump chamber 106a of the housing 106. The membrane 522 enables the air to pass through the bores 448, but prevents the passage of fluid, such as water, through the bores 448. Thus, the pressure management system 520 manages the pressure within the fluid reservoir system 118 by enabling the venting of air from the reservoir chamber 422 through the bores 448, while preventing the ingress of fluid, such as water, into the bores 448.

With reference to FIGS. 13 and 14, a pressure management system 620 is shown. As the pressure management system 620 can be used with the fluid infusion device 100 discussed with regard to FIGS. 1-8, only the pressure management system 620 will be discussed in detail herein.

In this example, the pressure management system 620 is defined in a portion of the housing 106 of the fluid infusion device 100. For example, the pressure management system 620 is defined in a reservoir chamber 622 of the housing 106 that receives the fluid reservoir 156 of the fluid reservoir system 118 (FIG. 2). The pressure management system 620 comprises an expandable member 624.

In one example, the expandable member 624 is defined as a portion of a wall 622*a* of the reservoir chamber 622, which has a thickness T, which is less than a thickness T2 and a thickness T3 of the remainder of the wall 622*a*. The reduced thickness T of the expandable member 624 enables the expandable member 624 to move or flex from a first, relaxed position (FIG. 13) to a second, expanded position (FIG. 14) to relieve pressure in the reservoir chamber 622. In other words, the expandable member 624 bulges outwardly from the remainder of the reservoir chamber 622, in a direction substantially opposite the fluid reservoir 156, to increase an available volume within the reservoir chamber 622. By increasing the available volume within the reservoir chamber 622, the pressure in the reservoir chamber 622 from the advancement of the slide 128 in the fluid reservoir 156 is reduced. Generally, the expandable member 624 extends over only a portion of the wall 622*a*, however, the expandable member 624 can extend over the entirety of the wall 622*a*, if desired. In addition, it should be noted that the expandable member 624 may be composed of the same material as a remainder of the wall 622*a*, or may be composed of a different, elastic material, in order to further increase the ability of the expandable member 624 to expand. Thus, the expandable member 624 illustrated herein is merely exemplary.

With the fluid reservoir 156 received in the reservoir chamber 622, as the drive screw 126 rotates, the slide 428 translates linearly. The advancement of the slide 428 decreases the volume of the reservoir chamber 622, which may result in an increase in the pressure in the reservoir chamber 622. As the pressure increases, in most instances, the pressure is relieved through the vents 164 of the connector body 154 (FIG. 8). In certain instances, the expandable member 624 moves from the first, relaxed position (FIG. 13) to the second, expanded position (FIG. 14) to increase the volume within the reservoir chamber 622 to relieve the pressure. By increasing the volume within the reservoir chamber 622, the pressure within the reservoir chamber 622 decreases. Thus, the pressure management system 620 manages the pressure within the fluid reservoir system 118 by increasing the volume within the reservoir chamber 622.

Figure 15:
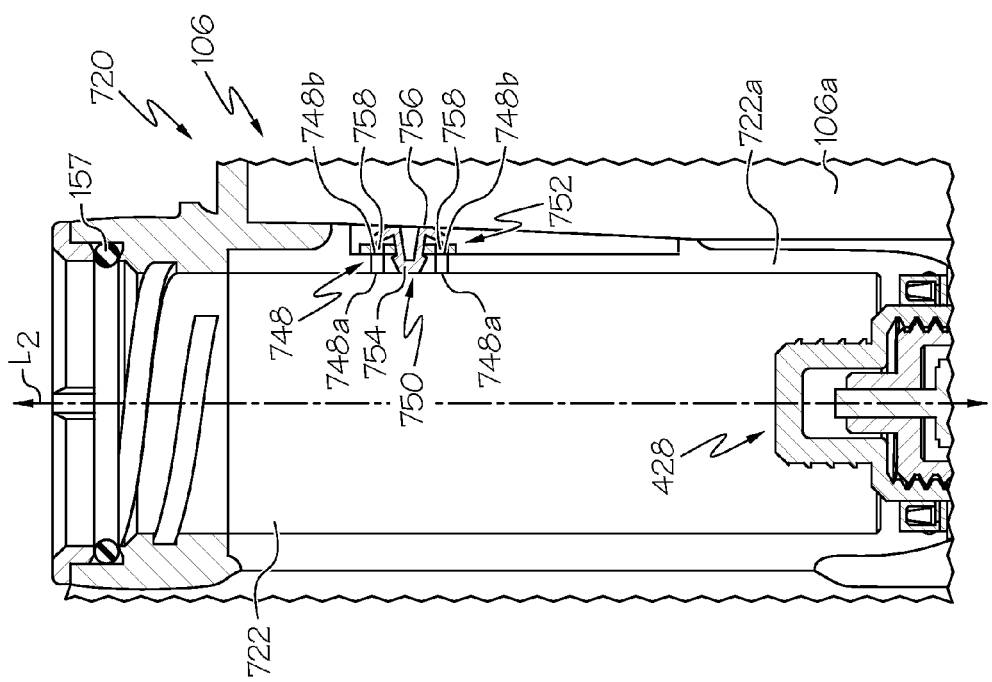
FIG. 15 is a schematic cross-sectional view of an exemplary pressure management system for use with the fluid infusion device of FIG. 1, in which the pressure management system is in a first position.
Figure 16:
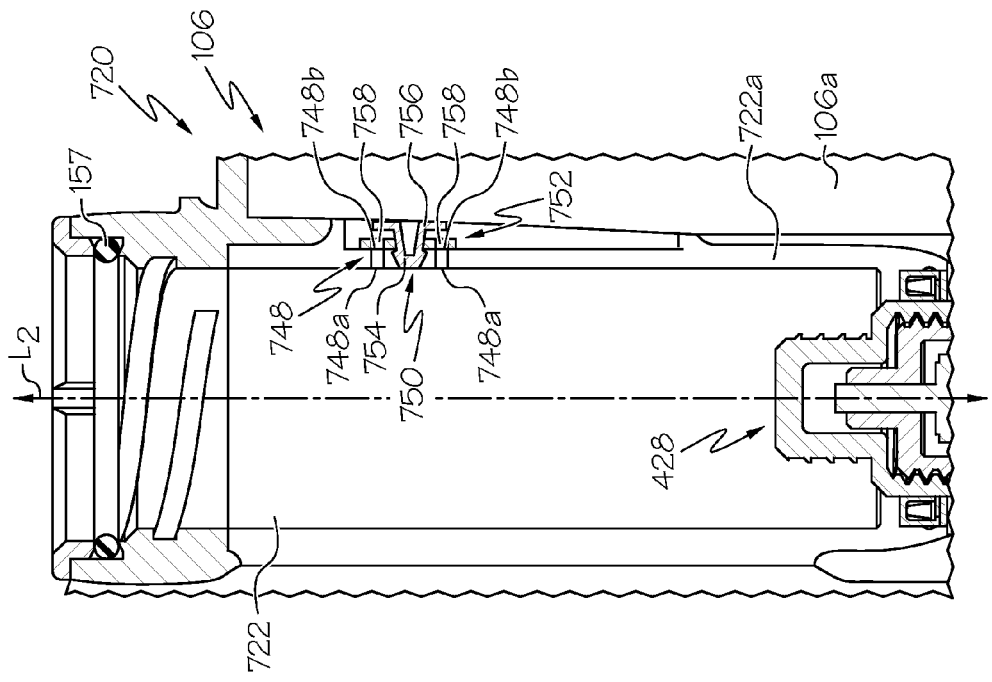
FIG. 16 is a schematic cross-sectional view of an exemplary pressure management system for use with the fluid infusion device of FIG. 1, in which the pressure management system is in a second position.

With reference to FIGS. 15 and 16, a pressure management system 720 is shown. As the pressure management system 720 can be used with the fluid infusion device 100 discussed with regard to FIGS. 1-8, only the pressure management system 720 will be discussed in detail herein.

In this example, the pressure management system 720 is coupled to a portion of the housing 106 of the fluid infusion device 100. For example, the pressure management system 720 is coupled to a reservoir chamber 722 of the housing 106 that receives the fluid reservoir 156 of the fluid reservoir system 118 (FIG. 2). The pressure management system 720 comprises one or more bores 748 and a valve 750.

The one or more bores 748 are defined in and through a wall 722*a* of the reservoir chamber 722. The bores 748 may be defined through the wall 722*a* in any desired pattern, and in one example, may be defined through the wall 722*a* of the reservoir chamber 722 such that a centerline of each bore 748 is substantially parallel to the longitudinal axis L2 of the reservoir chamber 722. The bores 748 may be arranged such that the bores 748 extend along the longitudinal axis L2 of the reservoir chamber 722, however, it should be noted that this arrangement of bores 748 is merely exemplary, as the bores 748 may be arranged offset from each other. In addition, it should be noted that while two bores 748 are illustrated herein, the pressure management system 720 can include any number of bores 748. The bores 748 can have any desired size or diameter, and the size or diameter may be varied amongst the bores 748 to enable tuning of the pressure management system 720 to the desired air flow rate. Moreover, while the bores 748 are illustrated herein as being cylindrical or with a circular perimeter, the bores 748 can have any desired polygonal shape, such as triangular or pentagonal, for example. Further, while the bores 748 are illustrated and described herein as being defined in the wall 722*a*, the bores 748 may be defined at any desirable location to within the reservoir chamber 722 to enable venting of the reservoir chamber 722. Thus, the location of the bores 748 is merely exemplary. A first end 748*a* of each of the bores 748 is in communication with the reservoir chamber 722 and an opposite, second end 748*b* of each of the bores 748 is in communication with the valve 750.

The valve 750 includes a valve seat 752, a valve stem 754 and a valve seal 756. In one example, the valve 750 comprises a check valve, but the valve 750 can comprise any suitable one-way valve, such as an umbrella valve or duckbill valve. The valve seat 752 is coupled to the wall 722*a* on a side of the wall 722*a* opposite the side of the wall 722*a* that contacts the fluid reservoir 156 when the fluid reservoir 156 is received in the reservoir chamber 722. The valve seat 752 may be coupled to the wall 722*a* through any suitable technique, such as ultrasonic welding, for example. The valve seat 752 defines one or more bores 758. Generally, the valve seat 752 defines substantially the same number of bores 758 as the number of bores 748. Thus, in this example, the valve seat 752 includes two bores 758. The bores 758 are defined in the valve seat 752 such that a centerline of a respective one of the bores 758 is coaxial with the centerline of a respective one of the bores 748 to enable communication between the bores 758 of the valve seat 752 and the bores 748. Generally, the second end 748*b* of each of the bores 748 is in communication with the respective one of the bores 758 to define an airflow path.

The valve stem 754 is coupled to the wall 722*a*. In one example, the valve stem 754 is fixedly coupled to the wall 722*a* such that the valve stem 754 does not interfere with or contact the fluid reservoir 156 when the fluid reservoir 156 is installed in the chamber 722. Thus, the valve stem 754 may be flush with the side of the wall 722*a* that contacts the fluid reservoir 156.

The valve seal 756 is coupled to the valve stem 754. The valve seal 756 is sized and shaped to seal the bores 758 of the valve seat 752. Generally, the valve seal 756 is composed of a resilient material such that the valve seal 756 is movable between a first, closed position (FIG. 15) and a second, opened position (FIG. 16) upon the pressure in the reservoir chamber 722 reaching a predefined pressure threshold. In the first, closed position, the valve seal 756 is sealing against the bores 758 and thereby blocking the airflow path created by the bores 748 and the bores 758 of the valve seat 752. In the second, opened position, the valve seal 756 is spaced apart from or deflected from the valve seat 752 such that the airflow path created by the bores 748 and bores 758 of the valve seat 752 is opened, allowing venting of air from the reservoir chamber 722 into the pump chamber 106*a* of the housing 106.

With the fluid reservoir 156 received in the reservoir chamber 722, as the drive screw 126 rotates, the slide 428 translates linearly. The advancement of the slide 428 decreases the volume of the reservoir chamber 722, which may result in an increase in the pressure in the reservoir chamber 722. Once the pressure reaches the predefined pressure threshold, the valve seal 756 moves from the first, closed position (FIG. 15) to the second, opened position (FIG. 16) to open the airflow path created by the bores 748 and bores 758 of the valve seat 752 to vent the reservoir chamber 722. Once the pressure in the reservoir chamber 722 drops below the predefined pressure threshold, the valve seal 756 moves from the second, opened position (FIG. 16) to the first, closed position (FIG. 15). Thus, the pressure management system 720 manages the pressure within the reservoir chamber 722 by enabling the venting of air from the reservoir chamber 722 through the bores 748 and bores 758 once the pressure in the reservoir chamber 722 reaches the predefined pressure threshold. Generally, the predefined pressure threshold is less than a static pressure necessary to move the stopper 172 within the fluid reservoir 156.

Figure 17:
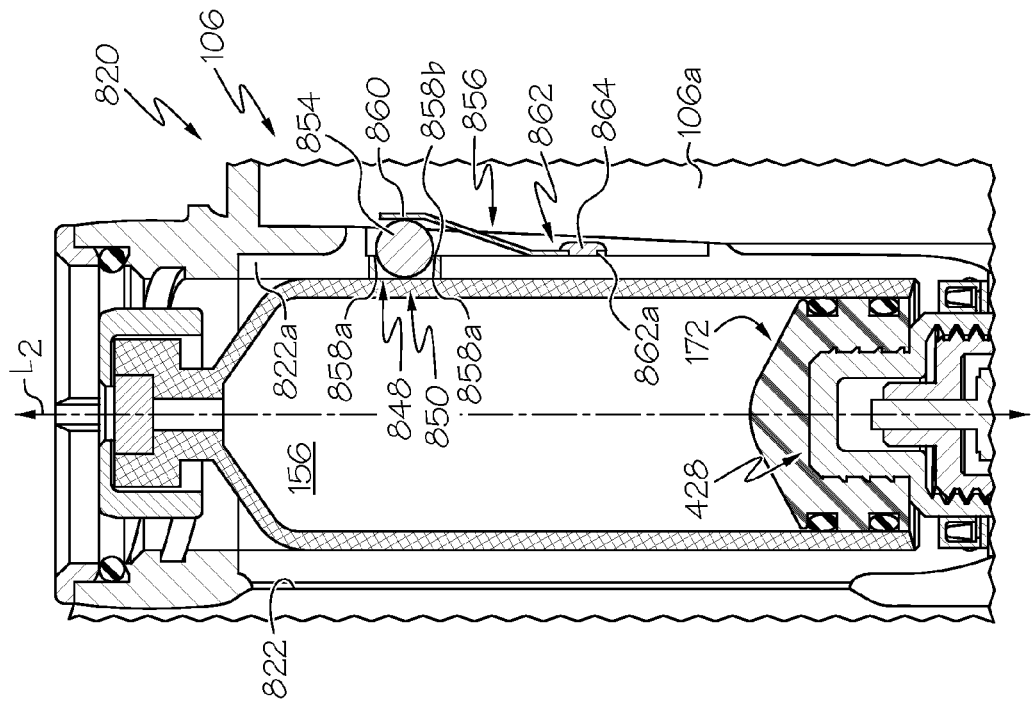
FIG. 17 is a schematic cross-sectional view of an exemplary pressure management system for use with the fluid infusion device of FIG. 1, in which the pressure management system is in a first position.
Figure 18:
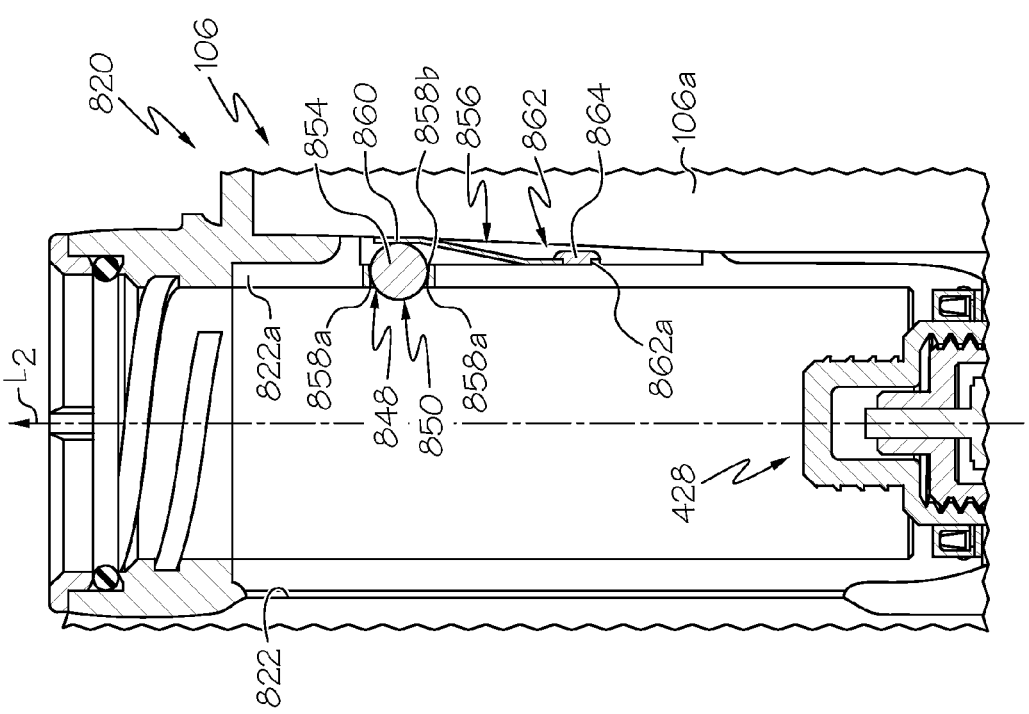
FIG. 18 is a schematic cross-sectional view of an exemplary pressure management system for use with the fluid infusion device of FIG. 1, in which the pressure management system is in a second position.

With reference to FIGS. 17 and 18, a pressure management system 820 is shown. As the pressure management system 820 can be used with the fluid infusion device 100 discussed with regard to FIGS. 1-8, only the pressure management system 820 will be discussed in detail herein.

In this example, the pressure management system 820 is coupled to a portion of the housing 106 of the fluid infusion device 100. For example, the pressure management system 820 is coupled to a chamber 822 of the housing 106 that receives the fluid reservoir 156 of the fluid reservoir system 118 (FIG. 2). The pressure management system 820 comprises one or more bores 848 and a valve 850.

The one or more bores 848 are defined in and through a wall 822a of the reservoir chamber 822. In this example, a single bore 848 is defined through the wall 822a, however, any number of bores 848 may be defined in the wall 822a in any desired pattern. The bore 848 is defined through the wall 822a of the reservoir chamber 822 such that a centerline of the bore 848 is substantially parallel to the longitudinal axis L2 of the reservoir chamber 822. The bore 848 can have any desired size or diameter, and while the bore 848 is illustrated herein as being cylindrical or with a circular perimeter, the bore 848 can have any desired polygonal shape, such as triangular or pentagonal, for example. Further, while the bore 848 is illustrated and described herein as being defined in the wall 822a, the one or more bores 848 may be defined at any desirable location to within the reservoir chamber 822 to enable venting of the reservoir chamber 822. Thus, the location of the bore 848 is merely exemplary. A first end 848a of the bore 848 is in communication with the fluid reservoir 156 when installed in the reservoir chamber 822 and an opposite, second end 848b of the bore 848 is in communication with the valve 850.

The valve 850 includes a valve seat 852, a valve stem 854 and a biasing member 856. The valve seat 852 is coupled to the wall 822a on a side of the wall 822a opposite the side of the wall 822a that contacts the fluid reservoir 156 when the fluid reservoir 156 is received in the reservoir chamber 822. The valve seat 852 may be coupled to the wall 822a through any suitable technique, such as ultrasonic welding, for example. The valve seat 852 is composed of any suitable material, and in one example, is composed of an elastomeric material. The valve seat 852 defines one or more bores 858. Generally, the valve seat 852 defines substantially the same number of bores 858 as the number of bores 848. Thus, in this example, the valve seat 852 includes one bore 858. The bore 858 is defined in the valve seat 852 such that a centerline of the bore 858 is coaxial with the centerline of the bore 848 to enable communication between the bore 858 of the valve seat 852 and the bore 848. Generally, the second end 848b of the bore 848 is in communication with the bore 858 to define an airflow path. The bore 858 is shaped to receive the valve stem 854. In one example, a first end 858a of the bore 858 has a diameter that is less than a diameter of a second end 858b of the bore 858. Thus, in this example, the bore 858 tapers from the second end 858b to the first end 858a to conform with the shape of the valve stem 854.

The valve stem 854 is received in the valve seat 852. In one example, the valve stem 854 is a spherical ball, however, the valve stem 854 can have any desired shape that cooperates with the valve seat 852. Thus, the valve stem 854 and the valve seat 852 illustrated herein are merely exemplary. The valve stem 854 is received within the valve seat 852 and is movable relative to the valve seat 852 and the wall 822a. Generally, the valve stem 854 is sized so as to extend outwardly from the valve seat 852 and the wall 822a, such that a portion of the valve stem 854 extends into the reservoir chamber 822. By extending into the reservoir chamber 822, the fluid reservoir 156 contacts the valve stem 854 upon insertion to move the valve stem 854 between a first, closed position (FIG. 17) and a second, opened position (FIG. 18). In the first, closed position, no airflow path exists between the reservoir chamber 822 and the housing 106. In the second, opened position, an airflow path exists from the reservoir chamber 822, through the bore 848, the bore 858 and into the pump chamber 106a of the housing 106.

The biasing member 856 is coupled to the valve stem 854 and the wall 822a. In one example, the biasing member 856 comprises a leaf spring, which includes a first end 860 and a second end 862. In this example, the first end 860 contacts the valve stem 854 and biases the valve stem 854 into the first, closed position. The second end 862 is fixedly mounted to the wall 822a. In this example, the second end 862 includes a bore 862a for receipt of a suitable coupling device, such as a mechanical fastener 864. It should be noted that the biasing member 856 can be coupled to the wall 822a through any suitable technique, and thus, the use of the mechanical fastener 864 is merely exemplary. Moreover, it should be noted that nay suitable biasing member could be employed to bias the valve stem 854 into the first, closed position, and thus, the use of a leaf spring is merely exemplary.

Upon insertion of the fluid reservoir 156 into the reservoir chamber 822, the fluid reservoir 156 contacts the valve stem 854 (FIG. 18). As the fluid reservoir 156 is moved into a final position in the reservoir chamber 822, the force of the insertion of the fluid reservoir 156 in the reservoir chamber 822 overcomes the force of the biasing member 856 and the valve stem 854 moves from the first, closed position (FIG. 17) to the second, opened position (FIG. 18). In the second, opened position, an airflow path between the reservoir chamber 822 and the pump chamber 106a of the housing 106 is created, thereby allowing the venting of air from the reservoir chamber 822. Once the fluid reservoir 156 is removed from the reservoir chamber 822, the biasing member 856 moves the valve stem 854 from the second, opened position to the first, closed position. Thus, the pressure management system 820 manages the pressure within the reservoir chamber 822 by enabling the venting of air from the reservoir chamber 822 through the bore 848 and bore 858 upon insertion of the fluid reservoir 156.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A fluid infusion device, comprising:
   a housing having a reservoir chamber that receives a fluid reservoir and a pump chamber;
   a drive system contained within the pump chamber of the housing and a slide of the drive system is movable relative to the fluid reservoir for dispensing fluid from the fluid reservoir;
   a seal disposed between the reservoir chamber and the pump chamber that defines an opening and the slide is movable relative to the seal through the opening; and
   a pressure management system at least partially defined in the slide of the drive system, the pressure management system including at least one air conduit that cooperates with the opening of the seal to vent air from the reservoir chamber into the pump chamber.

2. The fluid infusion device of claim 1, wherein the at least one air conduit comprises at least one dimple defined in the slide and the movement of the slide relative to the opening creates an airflow path to vent the reservoir chamber.

3. The fluid infusion device of claim 2, wherein the at least one dimple comprises a plurality of dimples defined in an exterior surface of the slide so as to be spaced apart along a longitudinal axis of the slide.

4. The fluid infusion device of claim 1, wherein the at least one air conduit comprises at least one slot defined in the slide and the movement of the slide relative to the opening creates an airflow path to vent air from the reservoir chamber.

5. The fluid infusion device of claim 4, wherein the at least one slot comprises a plurality of slots defined in an exterior surface of the slide so as to be spaced apart along a longitudinal axis of the slide.

6. The fluid infusion device of claim 1, further comprising the fluid reservoir and a connector body coupled to the housing and the fluid reservoir to define a fluid path from the housing, the connector body including one or more vents to vent air from the chamber.

7. The fluid infusion device of claim 1, wherein the fluid infusion device is an insulin infusion device.

8. A fluid infusion device, comprising:
   a housing having a reservoir chamber and a pump chamber;
   a fluid reservoir contained within the reservoir chamber of the housing;
   a connector body coupled to the housing and the fluid reservoir to define a fluid flow path out of the housing, the connector body including one or more vents to vent air from the reservoir chamber;
   a drive system contained within the pump chamber of the housing and coupled to the fluid reservoir, the drive system including a slide movable relative to the fluid reservoir to dispense fluid from the fluid reservoir;
   a seal disposed between the reservoir chamber and the pump chamber that defines an opening and the slide is movable relative to the seal through the opening; and
   a pressure management system at least partially defined in the slide of the drive system, the pressure management system including at least one air conduit that cooperates with the opening of the seal to vent air from the reservoir chamber into the pump chamber.

9. The fluid infusion device of claim 8, wherein the at least one air conduit comprises a plurality of recesses defined in an exterior surface of the slide so as to be spaced apart along a longitudinal axis of the slide.

10. The fluid infusion device of claim 8, wherein the at least one air conduit comprises a plurality of slots defined in an exterior surface of the slide so as to be spaced apart along a longitudinal axis of the slide.

11. The fluid infusion device of claim 8, wherein the fluid infusion device is an insulin infusion device.

* * * * *